US011266067B2

(12) United States Patent
Ko et al.

(10) Patent No.: US 11,266,067 B2
(45) Date of Patent: Mar. 8, 2022

(54) MOVING ROBOT, METHOD FOR CONTROLLING MOVING ROBOT, AND MOVING ROBOT SYSTEM

(71) Applicant: LG Electronics Inc., Seoul (KR)

(72) Inventors: Kyoungsuk Ko, Seoul (KR); Koh Choi, Seoul (KR); Sungwook Lee, Seoul (KR); Hyungsub Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 215 days.

(21) Appl. No.: 16/526,260

(22) Filed: Jul. 30, 2019

(65) Prior Publication Data
US 2020/0037498 A1 Feb. 6, 2020

Related U.S. Application Data

(60) Provisional application No. 62/714,746, filed on Aug. 5, 2018, provisional application No. 62/714,088, filed on Aug. 3, 2018.

(30) Foreign Application Priority Data

Jan. 31, 2019 (KR) ........................ 10-2019-0012990

(51) Int. Cl.
*A01D 34/00* (2006.01)
*G05D 1/02* (2020.01)
(52) U.S. Cl.
CPC ......... *A01D 34/008* (2013.01); *G05D 1/0212* (2013.01); *G05D 1/0274* (2013.01); *G05D 2201/0208* (2013.01)
(58) Field of Classification Search
CPC combination set(s) only.
See application file for complete search history.

(56) References Cited

U.S. PATENT DOCUMENTS 9,788,153 B1 * 10/2017 Newstadt .............. G06F 3/1219
2009/0043462 A1 * 2/2009 Stratton ................ E02F 9/2033
701/50
(Continued)

FOREIGN PATENT DOCUMENTS

CN 106171248 A 12/2016
CN 108142070 A 6/2018
(Continued)

OTHER PUBLICATIONS

European Search Report received from the European Patent Office (EPO) in European Patent Application No. 19189646.3, dated Apr. 24, 2020 (10 pages).
(Continued)

*Primary Examiner* — Jeff A Burke
*Assistant Examiner* — Arslan Azhar
(74) *Attorney, Agent, or Firm* — Finnegan, Henderson, Farabow, Garrett & Dunner LLP

(57) ABSTRACT

The present disclosure relates to a moving robot, a control method thereof, and a moving robot system. A moving robot according to the present disclosure includes a main body, a traveling unit configured to move the main body, a communication unit configured to communicate with a terminal and a location information transmitter, and a control unit configured to set a travel area using location information based on a signal received from the location information transmitter. The control unit is configured to recognize a location of the terminal. When location information regarding a target point within the boundary, pointed by the terminal at the recognized location, is received, the control unit is configured to store the location information. Also, the control unit is configured to control a traveling unit to move in the travel area while avoiding a predetermined area comprising coordinates matching the stored location information.

17 Claims, 18 Drawing Sheets

(56) References Cited

U.S. PATENT DOCUMENTS

| | | | |
|---|---|---|---|
| 2013/0041526 A1 | 2/2013 | Ouyang | |
| 2014/0196967 A1 | 7/2014 | Chang et al. | |
| 2016/0026185 A1* | 1/2016 | Smith | G05D 1/0259 356/614 |
| 2016/0059875 A1 | 3/2016 | Segman et al. | |
| 2016/0174459 A1 | 6/2016 | Balutis et al. | |
| 2016/0363933 A1* | 12/2016 | Balutis | G05D 1/0044 |
| 2016/0366818 A1 | 12/2016 | Ouyang | |
| 2016/0379164 A1* | 12/2016 | Li | H04L 67/18 705/333 |
| 2017/0150676 A1 | 6/2017 | Yamauchi et al. | |
| 2019/0208979 A1* | 7/2019 | Bassa | G06K 9/00664 |
| 2020/0037499 A1 | 2/2020 | Ko et al. | |
| 2020/0041601 A1 | 2/2020 | Ko et al. | |

FOREIGN PATENT DOCUMENTS

| | | |
|---|---|---|
| CN | 108307767 A | 7/2018 |
| DE | 102015218225 A1 | 4/2016 |
| EP | 2732687 A1 | 5/2014 |
| EP | 3073346 A1 | 9/2016 |
| EP | 3200040 A1 | 8/2017 |
| EP | 3561627 A1 | 10/2019 |
| FR | 3043304 A1 | 5/2017 |
| JP | 2017-531423 A | 10/2017 |
| KR | 10-2001-0009583 A | 2/2001 |
| KR | 10-2004-0081629 A | 9/2004 |
| KR | 10-2007-0061218 A | 6/2007 |
| KR | 10-2007-0109748 A | 11/2007 |
| KR | 10-2009-0011418 A | 2/2009 |
| KR | 10-2013-0014105 A | 2/2013 |
| KR | 10-2014-0066850 A | 6/2014 |
| KR | 10-2014-0073657 A | 6/2014 |
| KR | 10-2016-0026293 A | 3/2016 |
| KR | 10-2016-0128124 A | 11/2016 |
| KR | 10-2016-0136131 A | 11/2016 |
| KR | 10-2016-0149562 A | 12/2016 |
| KR | 10-2017-0073162 A | 6/2017 |
| KR | 10-1742913 | 6/2017 |
| KR | 10-2017-0082006 A | 7/2017 |
| KR | 10-2017-0082016 A | 7/2017 |
| KR | 10-2018-0038879 A | 4/2018 |
| KR | 10-2018-0069237 A | 6/2018 |
| KR | 10-2018-0085309 A | 7/2018 |
| WO | WO 2015/072896 A1 | 5/2015 |
| WO | WO 2015/192902 A1 | 12/2015 |
| WO | WO 2016/057140 A1 | 4/2016 |
| WO | WO 2016/097900 A1 | 6/2016 |
| WO | WO 2016/160376 A1 | 10/2016 |
| WO | WO 2018/108179 A1 | 6/2018 |
| WO | WO 2018/132048 A1 | 7/2018 |

OTHER PUBLICATIONS

Australian Office Action received from the Australian Patent Office in Australian Patent Application No. 2019208265, dated May 6, 2020 (6 pages).
Korean Office Action received from the Korean Intellectual Property Office in Korean Application No. 10-2019-0012990, dated Jul. 9, 2020 (14 pages).
Korean Office Action received from the Korean Intellectual Property Office in Korean Application No. 10-2019-0012989, dated Jul. 9, 2020 (17 pages).
Li et al., MDPI 2017 Creative Commons Attribution entitled "An Approach to Improve the Positioning Performance of GPS/INS/UWBB Integrated System with Two-Step Filter", Dec. 23, 2017 (14 pages).
Leonard et al., IEEE Transactions on Robotics and Automation, vol. No. 3 entitled "Mobile Robot Localization by Tracking Geometric Beacons" dated Jun. 1991 (7 pages).
Korean Office Action in Application No. KR 10-2019-0068832 dated Jul. 30, 2020 (5 pages).
Korean Office Action in Application No. KR 10-2019-0050058 dated Nov. 16, 2020 (5 pages).
Korean Office Action in Application No. KR 10-2019-0012994 dated Jul. 25, 2020 (19 pages).
Korean Notice of Allowance received from the Korean Intellectual Property Office in Korean Application No. 10-2019-0012989, dated Jan. 25, 2021 (2 pages).
Korean Notice of Allowance received from the Korean Intellectual Property Office in Korean Application No. 10-2019-0012994, dated Mar. 22, 2021 (3 pages).
U.S. Appl. No. 16/526,314, filed Jul. 30, 2019.
U.S. Appl. No. 16/531,222, filed Aug. 5, 2019.
U.S. Appl. No. 17/265,671, filed Feb. 3, 2021.
U.S. Appl. No. 17/265,590, filed Feb. 3, 2021.
U.S. Appl. No. 17/265,633, filed Feb. 3, 2021.
U.S. Appl. No. 17/265,613, filed Feb. 3, 2021.
U.S. Appl. No. 17/265,761, filed Feb. 3, 2021.
U.S. Appl. No. 17/266,481, filed Feb. 5, 2021.
U.S. Appl. No. 17/266,457, filed Feb. 3, 2021.
Extended European search report for corresponding European application No. 19189643.0, dated Dec. 20, 2019 (6 pages).
European Search Report received from the European Patent Office (EPO) in European Patent Application No. 19189641.4, dated Dec. 17, 2019 (8 pages).
Intellectual Property Australian Examination Report for Australian Application No. 2019210641 dated Oct. 8, 2020 (7 pages).
Korean Notice of Allowance received from the Korean Intellectual Property Office in Korean Application No. 10-2019-0050956, dated Jul. 19, 2021 (2 pages).
Korean Notice of Allowance received from the Korean Intellectual Property Office in Korean Application No. 10-2019-0050959, dated May 27, 2021 (2 pages).

* cited by examiner

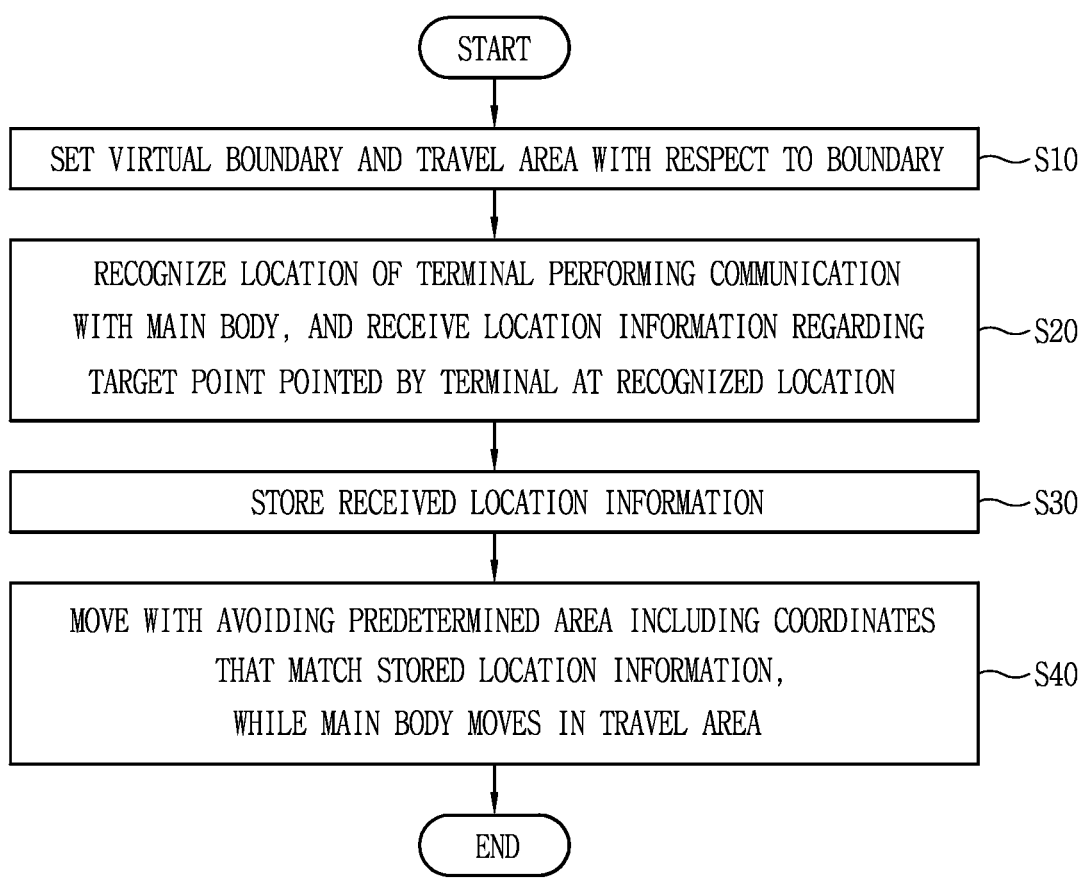

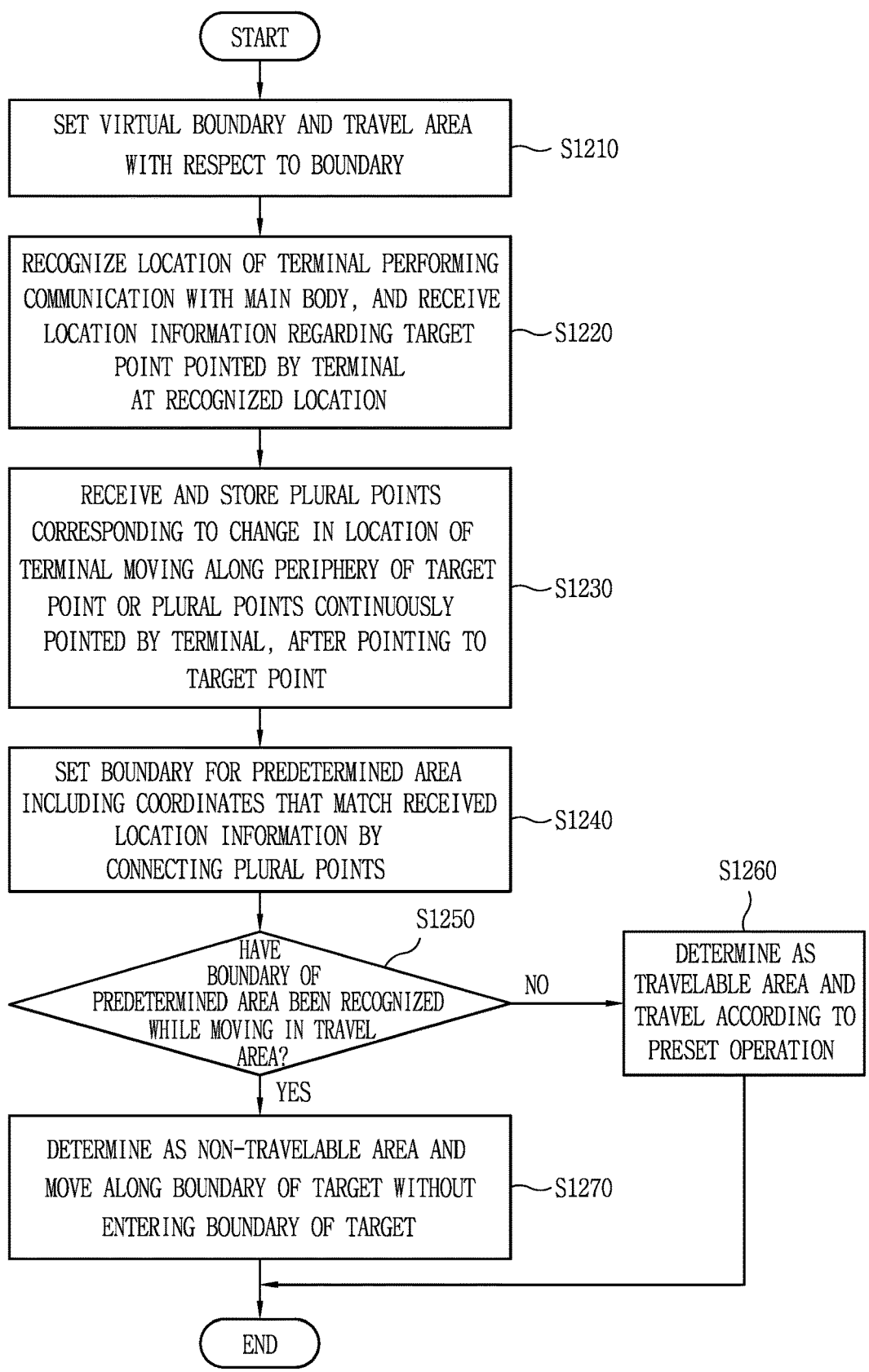

MOVING ROBOT, METHOD FOR CONTROLLING MOVING ROBOT, AND MOVING ROBOT SYSTEM

CROSS-REFERENCE TO RELATED APPLICATION

The present application claims priority under 35 U.S.C. § 119(a) to U.S. Provisional Patent Application No. 62/714,088, filed on Aug. 3, 2018, U.S. Provisional Patent Application No. 62/714,746, filed on Aug. 5, 2018, and Korean Patent Application No. 10-2019-0012990, filed on Jan. 31, 2019, the disclosures of which are hereby incorporated by reference in their entireties.

BACKGROUND OF THE DISCLOSURE

1. Field of the Disclosure

The present disclosure relates to a moving robot that autonomously travels in a designated area, a method for controlling the moving robot, and a moving robot system.

2. Description of the Related Art

Generally, a moving robot is a device that automatically performs a predetermined operation while traveling by itself in a predetermined area without a user's operation. The moving robot senses obstacles located in the area and performs its operations by moving close to or away from such obstacles.

Such a moving robot may include a cleaning robot that carries out cleaning while traveling in an area, as well as a lawn mower robot that mows the grass on a bottom of the area.

Generally, a lawn mower includes a passenger type lawn mower, which a user boards and controls to mow the lawn or cut the grass during movement, and a work-behind type lawn mower or hand-operating type lawn mower, which are pulled or pushed manually by a user to cut the grass. Such lawn mowers are moved by a direct control of the user to mow the lawn, which causes user's inconvenience in that the devices are operated directly by the user.

Accordingly, a moving robot type lawn mower that has an element for mowing the lawn provided on a moving robot, namely, a lawn mower robot, has been studied. However, since the lawn mower robot operates outdoors rather than indoors, it is necessary to set an area to be moved in advance. Specifically, since the outdoors is an open space unlike the indoors, an area designation should first be carried out, and an area to be driven by the robot should be limited to a space where grass is growing.

For this purpose, in Korean Patent Laid-Open Publication No. 2015-0125508, wires are laid under the ground where grass is planted in order to set an area to be moved by a lawn mower robot or a moving robot, and the moving robot is controlled to move in an inner area of the wires. Then, a boundary for the moving robot is set based on a voltage value induced by the wires.

However, this method has a problem that the wires must be laid under the ground every time to set the boundary. In addition, in order to change the boundary once set, new wires must be laid after the previously laid wires are removed, which increases the time and effort to set the boundary.

In order to solve this problem, a method of restricting the travel of a moving robot by setting a virtual wall in a manner of transmitting a signal through Beacon technology has been studied. However, since such a virtual wall can be set only linearly, it is not suitable for an outdoor area having various shapes of terrains. In addition, a plurality of ancillary devices for setting a virtual wall is required, which increases the cost. There is also a limitation in that the virtual wall cannot be set over all areas.

In addition, a method of restricting the travel of a moving robot based on GPS-based positioning is known to have an average error of about 2 to 5 m, which fails to satisfy the minimum positioning error range of about 30 cm required for autonomous travel. Also, even when sensors such as DGPSs, cameras, LiDARs, Raders and the like are used to reduce the average error of the GPS, blind zones and high cost are caused, and thus, those sensors are difficult to be commercialized in general.

Meanwhile, beacon-based positioning may be used to overcome the disadvantages of the GPS-based positioning.

In this regard, the U.S. Patent laid-open Publication No. US 2017/0026818 discloses a method in which a mobile lawn mower robot is paired with Beacon. A distance between the Beacon and the mobile lawn mower robot is determined, and it is determined whether the Beacon is located within a pairing distance by comparing the determined distance with the pairing distance. The result of the determination is used for a navigator. However, there are drawbacks and security issues because related applications need to be installed to use the Beacon and pairing needs to be carried out.

Recently, a method of restricting the travel of a moving robot by using a low-cost Ultra-Wideband (UWB) communication technology known to have precision of about 30 cm or shorter has been studied. Ultra-Wideband (UWB) is suitable for real-time positioning because it is hardly affected by multipath problems by virtue of its properties of precise region estimation and material penetration.

Even after boundary setting for the moving robot is performed, the set boundary may be changed by the various obstacles installed or fixed within the boundary.

On the other hand, unlike an indoor floor, an outdoor surface is uneven and this makes it difficult to smoothly change a travel path (driving path, travel route, etc.). This is especially true when new obstacles are encountered while traveling. Accordingly, it is preferable that obstacles existing within a set boundary are registered in advance through a map or the like before the moving robot makes actual traveling or when test traveling of the moving robot is carried out.

On the other hand, in the case of the outdoor surface, temporary obstacles such as temporary fixtures and the like as well as fixed obstacles may exist. In the case of a temporary obstacle, it is changed in location or removed/reinstalled as necessary. Accordingly, when the temporary obstacle is registered on a map or the like in the same manner as the fixed obstacle, time and effort required may be increased and inconvenience may be aggravated.

SUMMARY OF THE DISCLOSURE

Therefore, one aspect of the present disclosure is to provide a moving robot, capable of achieving user convenience and smooth travel by distinguishing a fixed obstacle and a temporary obstacle when registering obstacles, a method for controlling the moving robot, and a moving robot system.

Another aspect of the present disclosure is to provide a moving robot, capable of quickly and easily registering location information and size information related to a target, such as a temporary obstacle, which should be temporarily avoided while the moving robot is traveling, in a different manner from a fixed obstacle, a method for controlling the moving robot, and a moving robot system.

Still another aspect of the present disclosure is to provide a moving robot, capable of acquiring and registering location information and size information related to a target, without requiring a terminal or the moving robot to a location of the target to be registered, a method for controlling the same, and a moving robot system.

Still another aspect of the present disclosure to provide a moving robot, capable of quickly removing information related to a target, which is temporarily installed and has been registered on a map, when the target is removed.

Accordingly, the present disclosure has implemented a method in which a fixed obstacle and a temporary obstacle are distinguished upon registration of obstacles for a moving robot, and location information regarding a point where a temporary obstacle is located, pointed by a terminal, is stored to facilitate fast registration of the temporary obstacle.

In the present disclosure, it has also been realized that size information regarding a temporary obstacle can be acquired by using location information related to a plurality of points pointed by a terminal or by receiving a change in location of the terminal moving around the temporary obstacle. At this time, the moving robot does not have to move to the location of the temporary obstacle.

In addition, in the present disclosure, it has been implemented that pre-stored location information related to a pointed point can be deleted or updated to a changed pointed point, so as to quickly reflect the location change of a temporary obstacle, in the case where the temporary obstacle is removed or moved to another location.

In this specification, the term 'target' defined herein may include the temporary obstacle and an object/location area desired to be set as a temporary non-travelable area. Also, the term 'target point' may indicate the location of the target and may be defined as the location/coordinates of the target pointed by a terminal.

A predetermined area including the coordinates of the target point may be defined as an area of a predetermined size centered on the coordinates of the target point. The predetermined area may be recognized as a non-travelable area in a travel area. The shape and size of the predetermined area may be determined by using location information regarding a plurality of points pointed by a terminal or by receiving changes in the location of the terminal moving around a temporary obstacle.

Specifically, a moving robot according to an embodiment of the present disclosure may include a main body, a traveling unit configured to move the main body, a communication unit configured to communicate with a terminal and a location information transmitter installed in an area to transmit a signal, and a control unit configured to set a travel area based on a virtual boundary when the virtual boundary is set using location information based on a signal received from the location information transmitter. The control unit may be configured to recognize a location of the terminal and store location information related to a target point, the target point being located within the boundary and pointed by the terminal at the recognized location, when the location information related to the target point is received. The control unit may also be configured to control the traveling unit such that the main body avoids a predetermined area comprising coordinates that match the stored location information, while moving in the set travel area.

Further, in one embodiment, the target point may correspond to single coordinates, pointed by the terminal, among a plurality of coordinates that match temporary obstacles or specific areas to be set as non-travelable areas within the travel area.

In one embodiment, the control unit may further be configured to recognize a current location of the terminal based on the signal transmitted from the location information transmitter, and receive, as the location information, coordinates of a target point, the coordinates being calculated relative to the recognized current location of the terminal.

In one embodiment, the control unit may further be configured to determine a current location of the main body based on the signal transmitted from the location information transmitter, and recognize coordinates of the target point corresponding to the received location information, based on the determined location of the main body and the location of the terminal existing within the virtual boundary.

In one embodiment, the control unit may further be configured to recognize coordinates of the target point corresponding to the location information with respect to a current location of the main body, based on a first point corresponding to a reference location pointed by the terminal at the current location of the terminal, and a second point corresponding to the target point pointed by the terminal at the current location after pointing to the first point.

In one embodiment, the second point may correspond to the coordinates of the target point calculated based on the terminal, the first point may correspond to coordinates one of the current location of the terminal, a location of the location information transmitter, a location of the moving robot, or a location of a charging station of the moving robot, and the initial posture value of the terminal may be set based on the first point before pointing to the second point.

In one embodiment, the control unit may further be configured to recognize coordinates of the target point corresponding to the location information with respect to a current location of the main body, based on a distance information from the location of the terminal to the target point pointed by the terminal, and a virtual trajectory generated based on the location of the terminal.

In one embodiment, the control unit may further be configured to set a boundary of the predetermined area based on a change in location of the terminal, the location of the terminal being movable along a periphery of the target point after pointing to the target point. The control unit may further be configured to control the traveling unit such that the main body moves along the boundary of the predetermined area and moves in the travel area, without entering the boundary of the predetermined area.

In one embodiment, the control unit may further be configured to set a boundary of the predetermined area by connecting a plurality of points continuously pointed by the terminal after pointing to the target point, and control the traveling unit such that the main body moves along the boundary of the predetermined area and moves in the travel area, without entering the boundary of the predetermined area.

In one embodiment, the control unit may further be configured to transmit the stored location information and the location information of the main body to the terminal.

In one embodiment, the control unit may further be configured to transmit at least one of size information or shape information associated with the target, based on a boundary of the predetermined area set based on a change in location of the terminal that is movable along a periphery of the target point after pointing to the target point.

In one embodiment, the control unit may further be configured to transmit at least one of size information or shape information associated with the target, based on a boundary of the predetermined area set by connecting a plurality of points continuously pointed by the terminal after pointing to the target point.

In one embodiment, the control unit may be further configured to update the stored location information to coordinates that match a changed target point, in response to a target point change request received from the terminal, and control the traveling unit such that a current location of the main body determined according to the signal of the location information transmitter while the main body is moving in the travel area is not included in a predetermined area comprising coordinates that match the updated located information.

In one embodiment, when an obstacle is detected near a predetermined area including coordinates that match the stored location information, the control unit may be further configured to control the traveling unit to move while avoiding a merged area generated by merging the predetermined area with the detected obstacle.

A moving robot system according to one embodiment of the present disclosure may include a location information transmitter installed in an area, the location information transmitter being configured to transmit a signal for recognizing location information, a moving robot configured to set a virtual boundary relative to location information based on a signal of the location information transmitter, and move in a travel area set on the basis of the boundary. The system may comprise a terminal configured to communicate with the location information transmitter within the virtual boundary, calculate location information regarding a pointed target point within the virtual boundary by using a signal, and transmit the location information to the moving robot. The mobile robot may be configured to store the transmitted location information regarding the target point and move in the travel area while avoiding a predetermined area comprising coordinates that match the stored location information.

In one embodiment, the terminal may be further configured to set a boundary of the predetermined area based on a change in location while moving along a periphery of the target point after pointing to the target point, and transmit information related to the set boundary of the predetermined area to the moving robot. The moving robot may be configured to move in the travel area while avoiding the boundary of the predetermined area.

In one embodiment, the terminal may further be configured to set a boundary of the predetermined area by connecting a plurality of points continuously pointed after pointing to the target point, and transmit information related to the boundary of the predetermined area to the moving robot. The moving robot may be configured to move in the travel area along the boundary of the predetermined area without entering the boundary of the predetermined area.

A method for controlling a moving robot according to one embodiment of the present disclosure may include setting a virtual boundary relative to location information based on a signal received from a location information transmitter so as to set a travel area based on the boundary, recognizing a location of a terminal configured to communicate with a main body, to receive location information regarding a target point pointed by the terminal at the recognized location of the terminal, storing the received location information, and moving in the travel area while avoiding a predetermined area comprising coordinates that match the stored location information.

Effects of the Disclosure

According to an embodiment of the present disclosure, in the case where there is a target, such as a temporary obstacle, which a moving robot has to temporarily avoid during travel, the target can be registered quickly using only a terminal, which can be moved quickly, without performing an avoidance design every time or making the moving robot travel along an outer periphery of the target. This may result in achieving user convenience and smooth travel of the moving robot.

In addition, since a location of a target can be calculated by simply pointing to the target by the terminal at a far distance without moving the terminal to the location of the target, the user's effort and time can be reduced.

In addition, acquisition of a size of a target and registration, change and removal of the target corresponding to the size can be simply performed selectively by making the terminal move along an outer periphery of the target or additionally pointing to corners of the target at a remote distance.

BRIEF DESCRIPTION OF THE DRAWINGS

FIG. 5 is a flowchart illustrating a method for controlling the moving robot that detects an obstacle existing within the boundary using the terminal and performs a corresponding traveling operation, in accordance with an embodiment of the present disclosure.

FIG. 12 is a flowchart illustrating an exemplary method for controlling a moving robot, in accordance with an embodiment of the present disclosure.

DETAILED DESCRIPTION OF THE DISCLOSURE

Hereinafter, a moving robot according to the present disclosure will be described in detail with reference to the accompanying drawings.

Hereinafter, description will be given in detail of embodiments disclosed herein. Technical terms used in this specification are merely used for explaining specific embodiments, and should not be constructed to limit the scope of the technology disclosed herein.

First, the term "moving robot" disclosed herein may have the same meaning as "robot" which can autonomously travel, "lawn mower moving robot," "lawn mower robot," "lawn mower," and "moving robot for mowing lawn," and those terms will be used interchangeably.

Figure 1:
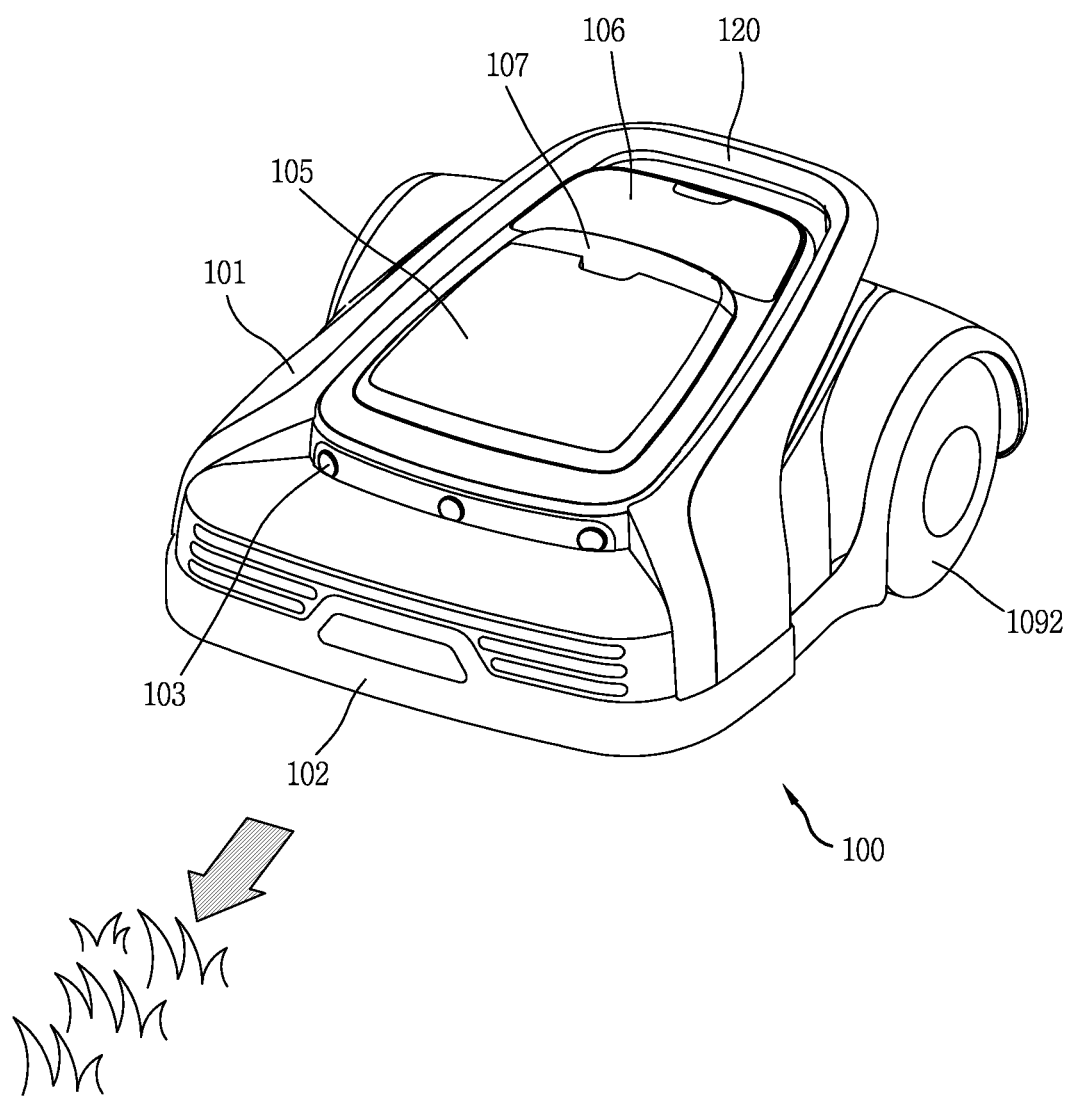
FIG. 1 is a perspective view illustrating an example of a moving robot according to the present disclosure.

FIG. 1 is a block diagram of a moving robot for mowing lawn according to the present disclosure.

A moving robot according to the present disclosure may include an outer cover 101, an inner body (not shown), and wheels 1092.

The outer cover 101 may define an appearance of the moving robot. The appearance of the moving robot may be formed in a shape similar to an automobile, for example. The outer cover 101 may be formed to cover an outside of the inner body (not shown).

The outer cover 101 may be mounted on an upper portion of the inner body so as to cover the upper portion of the inner body. A receiving portion may be formed inside the outer cover 101, and the inner body may be received in the receiving portion.

A bumper 102 may be provided on a front portion of the outer cover 101 in preparation for collision with an obstacle. The bumper 102 may be formed of a rubber material that can mitigate impact.

A plurality of ultrasonic sensor modules 103 may be mounted on a front upper portion of the outer cover 101. The plurality of ultrasonic sensor modules 103 may be configured to emit ultrasonic waves toward the front of the robot while the robot travels, and receive reflected waves reflected from the obstacle, so as to detect the front obstacle.

The plurality of ultrasonic sensor modules 103 may be spaced apart from one another in a vehicle width direction. The plurality of ultrasonic sensor modules 103 may be spaced apart from the bumper 102 rearward by a predetermined distance. In addition, the plurality of ultrasonic sensor modules 103 may be replaced with other signal-based sensors, such as UWB sensors, other than the ultrasonic sensors.

The moving robot may include a control unit. The control unit may stop the operation of the moving robot when an obstacle is detected by receiving a detection signal from the ultrasonic sensor modules 103.

A first top cover 105 and a second top cover 106 may be provided on the top of the outer cover 101. A stop switch 107 may be provided between the first top cover 105 and the second top cover 106. The stop switch 107 may be mounted on the outer cover 101 and may be pressed by the user. When the user presses the stop switch 107 one time in an emergency state, the stop switch 107 may be switched on so that the operation of the moving robot is stopped. When the stop switch 107 is pressed once more, the operation of the moving robot may be restarted.

The plurality of wheels 1092 may be connected to respective driving motors provided in the inner body, and rotatably mounted on both side surfaces of the inner body 160 in a widthwise direction of the inner body 160. Each of the plurality of wheels 1092 may be connected to the driving motors by a driving shaft, so as to be rotatable by receiving power from the driving motors.

The plurality of wheels 1092 may supply power for the travel of the robot, and each of the plurality of wheels 1092 may be controlled by the control unit independently such that the wheels 1092 can be rotated at different RPM.

In addition, a handle 120 (which may also be referred to as a 'carrying handle') may be installed on the outer cover 101 so that the user can grip it with a hand while carrying the moving robot.

Figure 2A:
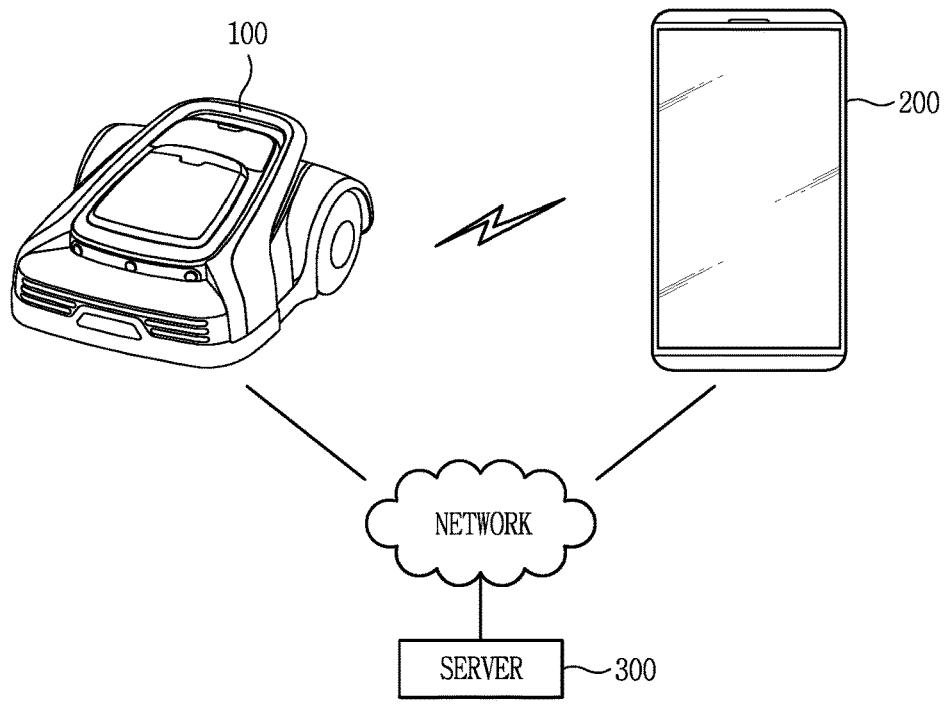
FIG. 2A is a conceptual view illustrating a state where the moving robot performs communications with a terminal and a server according to the present disclosure.

FIG. 2A illustrates a state where the moving robot 100 according to the present disclosure performs communications with a terminal 200 and a server 300. The moving robot 100 according to the present disclosure may exchange data with the terminal 200 through network communication. In addition, the moving robot 100 may perform a weeding-related operation or a corresponding operation according to a control command received from the terminal 200 through network communication or other communication.

Here, the network communication may refer to at least one of wireless communication technologies, such as a wireless LAN (WLAN), a wireless personal area network (WPAN), a wireless fidelity (Wi-Fi) Wi-Fi direct, Digital Living Network Alliance (DLNA), Wireless Broadband (WiBro), World Interoperability for Microwave Access (WiMAX), Zigbee, Z-wave, Blue-Tooth, Radio Frequency Identification (RFID), Infrared Data Association (IrDA), Ultrawide-Band (UWB), Wireless Universal Serial Bus (USB), and the like.

The illustrated network communication may vary depending on a communication method of the moving robot 100.

In FIG. 2A, the moving robot 100 may provide information sensed through each sensing unit to the terminal 200 through network communication. In addition, the terminal 200 may transmit a control command generated based on the received information to the moving robot 100 through the network communication.

On the other hand, the terminal 200 may be named as a controller, a remote controller, or the like, which is manipulated by a user to control operations related to the travel of the moving robot 100. To this end, the terminal 200 may be provided with an application installed therein for controlling operations related to the travel of the moving robot 100, and the corresponding application may be executed through a user operation.

In FIG. 2A, a communication unit of the moving robot 100 and a communication unit of the terminal 200 may also directly communicate with each other or indirectly communicate with each other via another router (not shown), to recognize information related to a traveling operation of the moving robot 100 and locations of the moving robot 100 and the terminal 200.

Also, the moving robot 100, the server 300, and the terminal 200 may be connected via a network and exchange data with one another.

For example, the server 300 may exchange data with the moving robot 100 and/or the terminal 200, to register information related to a boundary set for the moving robot 100, map information based on the set boundary, and/or obstacle information on the map. In addition, the server 300 may provide the registered information to the moving robot 100 and/or the terminal 200 according to a request.

The server 300 may be wirelessly connected to the moving robot 100 through the terminal 200. Alternatively, the server 300 may be connected to the moving robot 100 without passing through the terminal 200.

The server 300 may include a programmable processor and may include various algorithms. By way of example, the server 300 may be provided with algorithms related to performing machine learning and/or data mining. As an example, the server 300 may include a speech recognition algorithm. In this case, when receiving voice data, the received voice data may be output by being converted into data in a text format.

Meanwhile, the server 300 may store firmware information and driving information (course information, and the like) for the moving robot 100, and register product information related to the moving robot 100. For example, the server 300 may be a server managed by a cleaner manufacturer or a server managed by an open application store operator.

Figure 2B:
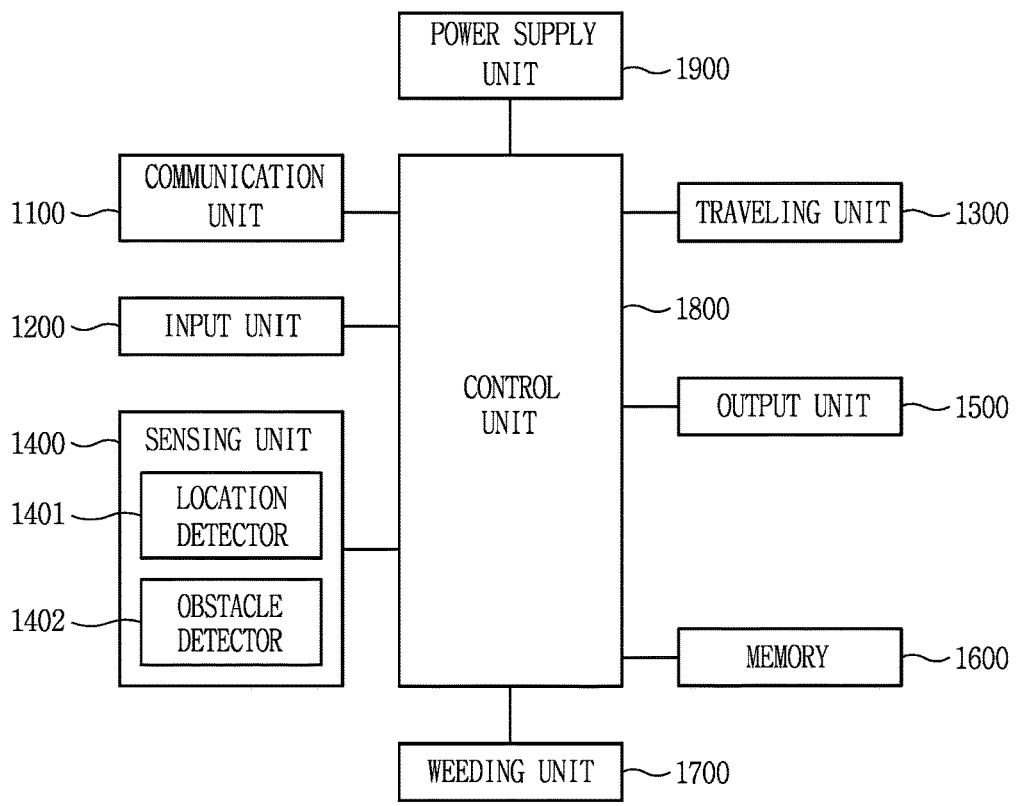
FIG. 2B is a block diagram illustrating an exemplary configuration of the moving robot according to the present disclosure.
Figure 2C:
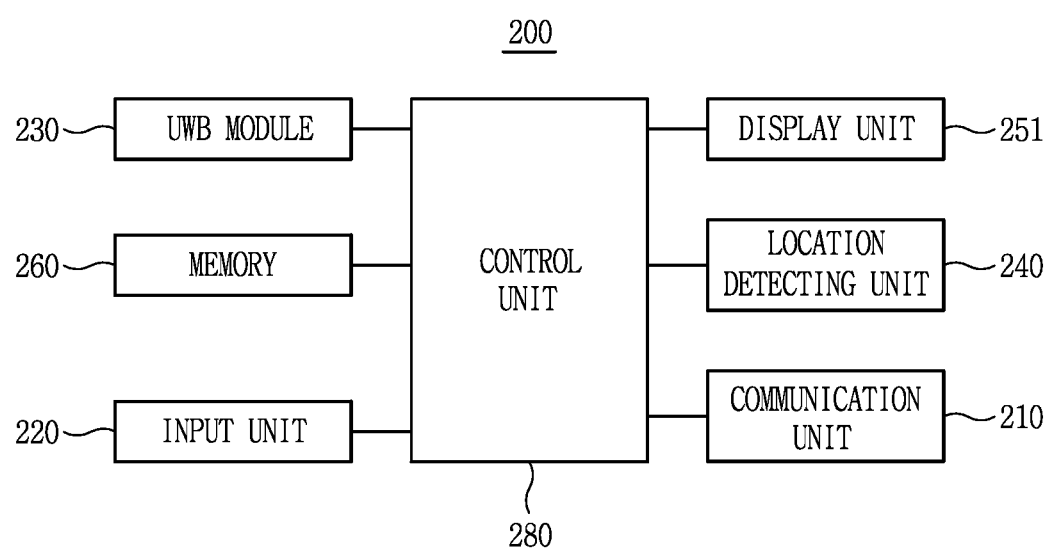
FIG. 2C is a block diagram illustrating an exemplary configuration of the terminal performing communication with the moving robot according to the present disclosure.

Hereinafter, FIG. 2B is a block diagram illustrating an exemplary configuration of the moving robot 100 according to the present disclosure, and FIG. 2C is a block diagram illustrating an exemplary configuration of the terminal 200 communicating with the moving robot 100.

First, the configuration of the moving robot 100 will be described in detail with reference to FIG. 2B.

As illustrated in FIG. 2B, the moving robot 100 may include a communication unit 1100, an input unit 1200, a traveling unit 1300, a sensing unit 1400 provided with a location detector 1401 and an obstacle detector 1402, an output unit 1500, a memory 1600, a weeding unit 1700, a control unit 1800, and a power supply unit 1900.

The communication unit 1100 may perform communication with the terminal 200 through a wireless communication scheme. Also, the communication unit 1100 may perform communication with the terminal which is connected to a predetermined network to control an external server or the moving robot.

The communication unit 1100 may transmit information related to a generated map to the terminal 200. The communication unit 1100 may receive a command from the terminal 200 and transmit data regarding an operation state of the moving robot 100 to the terminal 200.

The communication unit 1100 may transmit and receive data by being equipped with a communication module such as Wi-Fi, WiBro, and the like, as well as through short-range wireless communications such as Zigbee and Bluetooth. In addition, the communication unit 1100 may include a UWB module for transmitting a UWB signal.

The input unit 1200 may include an input element such as at least one button, a switch, and/or a touch pad. The output unit 1500 may include an output element such as a display unit and a speaker. When the output unit 1500 is used simultaneously as the input element and the output element, a user command can be input and the operation state of the moving robot can be output through the display unit and the speaker.

The memory 1600 may store therein an input detection signal, reference data for determining an obstacle, and obstacle information regarding a detected obstacle. The memory 1600 may also store therein control data for controlling the operation of the moving robot and data according to a cleaning mode of the moving robot.

The memory 1600 may store therein collected location information, and information related to a travel area and its boundary. For example, the memory 1600 may store data that is readable by a microprocessor, and may be one of a hard disk drive (HDD), a solid state disk (SSD), a silicon disk drive (SDD), ROM, RAM, CD-ROM, a magnetic tape, a floppy disk, or an optical data storage device.

The traveling unit 1300 may include at least one driving motor, and may allow the moving robot to move according to a control command of the control unit 1800. The traveling unit 1300 may include a left wheel driving motor for rotating the left wheel and a right wheel driving motor for rotating the right wheel. In addition, the traveling unit 1300 may further include one or more auxiliary wheels for stable support.

For example, while the moving robot main body travels, the left wheel driving motor and the right wheel driving motor may be rotated in the same direction. However, a traveling direction of the moving robot main body (or moving robot) 100 may be switched when the left wheel driving motor and the right wheel driving motor are rotated at different speeds or in opposite directions.

The weeding unit 1700 may cut the lawn on a bottom surface while the moving robot is traveling. The weeding unit 1700 may be provided with a brush or blade for cutting the lawn, and may cut the lawn on the bottom surface in a rotating manner.

The obstacle detector 1402 may include a plurality of sensors for detecting obstacles existing in front of the moving robot. The obstacle detector 1402 may detect obstacles in front of the main body, namely, in the traveling direction of the moving robot, using at least one of a laser, ultrasonic waves, infrared rays, or a 3D sensor.

In addition, the obstacle detector 1402 may include a camera for capturing the front of the moving robot so as to detect an obstacle. The camera may be a digital camera, which may include an image sensor (not shown) and an image processor (not shown). An image sensor may be an apparatus for converting an optical image into an electrical signal. The image sensor may be configured as a chip on which a plurality of photo diodes is integrated, and the photodiode may be a pixel, for example. Electric charges are accumulated in the respective pixels by an image, which is formed on the chip by light passing through a lens, and the electric charges accumulated in the pixels are converted into an electrical signal (for example, voltage). Charge Coupled Device (CCD), Complementary Metal Oxide Semiconductor (CMOS), and the like are well known as image sensors. In addition, a DSP or the like may be provided as the image processor.

The location detector 1401 may include a plurality of sensor modules for transmitting and receiving location information. The location detector 1401 may include a GPS module that transmits and receives GPS signals or a location sensor module that transmits and receives location information to and from a location information transmitter 50 (see FIG. 3). For example, the location detector 1401 may be provided with a sensor module that transmits and receives an ultrasonic, UWB, or infrared signal when the location information transmitter transmits a signal through one of ultrasonic wave, ultra-wide band (UWB), and/or infrared ray.

When the location sensor module is implemented as a UWB sensor module, even if an obstacle exists between the location information transmitter 50 and the moving robot 100, signals can be transmitted and received through such an obstacle or the like. Therefore, transmission and reception of the UWB signals may be smoothly carried out.

Unless otherwise mentioned, it may be premised that the location information transmitter 50 and the moving robot 100, the location information transmitter 50 and the terminal 200, and the moving robot 100 and the terminal 200 are provided with at least one UWB sensor module so as to transmit and receive the UWB signals to and from each other.

Also, even when the moving robot 100 moves while following the terminal 200, the location may be determined using the sensor module.

For example, when the moving robot 100 travels while following the terminal 200, the terminal 200 and the moving robot 100 each may include a UWB sensor and may perform wireless communication with each other. The terminal may transmit a signal from its UWB sensor. The moving robot may receive the signal of the terminal through its UWB sensor and determine the location of the terminal based on the signal of the terminal so as to follow the terminal.

As described above, since the UWB signal transmitted by the UWB sensor can pass through an obstacle, the signal transmission may not be affected even if the user moves while holding the terminal. However, in the case of an obstacle having a designated size or more, the signal transmission may fail or a signal transmission distance may be reduced even if the signal is transmitted through the obstacle.

In addition, the UWB sensors provided in the terminal and the moving robot, respectively, may estimate or measure a distance between them. When the moving robot follows the terminal, the travel of the moving robot may be controlled according to a distance from the terminal so that the moving robot does not move away from the terminal by a designated distance. That is, the moving robot may follow the terminal while maintaining a proper distance so that the distance from the terminal is not too close or too far away.

The location detector 1401 may include one UWB sensor or a plurality of UWB sensors. For example, when the location detector 1401 includes two UWB sensors, for example, the two UWB sensors may be provided on left and right sides of the main body of the moving robot, respectively, to receive signals. Accordingly, the location detector 1401 may detect the location by comparing the received signals.

For example, when the distances measured respectively by the left sensor and the right sensor are different according to the locations of the moving robot and the terminal, relative locations of the moving robot and the terminal and a direction of the moving robot may be determined based on the distances.

Meanwhile, in addition to the obstacle detector 1402 and the location detector 1401, the sensing unit 1400 may include various sensors, such as a cliff detection sensor installed on a rear surface of the main body to detect a cliff, a rain sensor to detect a humid or rainy weather condition, a proximity sensor, a touch sensor, an RGB sensor, a fuel gauge sensor, an acceleration sensor, a geomagnetic sensor, a gravity sensor, a gyroscope sensor, an illuminance sensor, an environmental sensor (a thermometer, a radiation detection sensor, a heat detection sensor, a gas detection sensor, etc.), a plurality of 360-degree sensors, a floor state detection sensor, and the like.

In addition, the sensing unit 1400 may include at least one tilt sensor (not shown) for detecting movement of the main body. The tilt sensor may calculate a tilted direction and a tilted angle of the main body when the main body is tilted in a front, rear, left, or right direction. The tilt sensor may be an acceleration sensor, or the like. In the case of the acceleration sensor, any of a gyro type, an inertial type, or a silicon semiconductor type may be applicable. In addition, various sensors or devices capable of detecting the movement of the main body may be used.

The control unit 1800 may control data input/output, and may control the traveling unit 1300 so that the moving robot travels according to settings. The control unit 1800 may control the traveling unit 1300 to independently control the operations of the left wheel driving motor and the right wheel driving motor, so that the main body of the moving robot 100 travels straight or rotates.

The control unit 1800 may determine a traveling direction corresponding to a signal received through the sensing unit 1400 and control the traveling unit 1300. In addition, the control unit 1800 may control the traveling unit 1300 to vary a traveling speed, so that the moving robot travels or stops according to the distance from the terminal. Accordingly, the moving robot can move while following locations of the terminal corresponding to the change in location of the terminal.

In addition, the control unit 1800 may control the moving robot to move, following the terminal 200, according to a set mode.

The control unit 1800 may set a virtual boundary for an area based on location information received from the terminal 200 or location information calculated through the location detector 1401. Also, the control unit 1800 may set any one of areas formed by set boundaries as a travel area. The control unit 1800 may set a boundary in a shape of a closed loop by connecting discontinuous location information with lines or curves, and may set an inner area of the set boundary as the travel area. Also, when a plurality of boundaries is set, the control unit 1800 may set any of areas formed by the plurality of boundaries as a travel area.

When the boundary and the travel area are set, the control unit 1800 may control the traveling unit 1300 so that the moving robot travels within the travel area without moving over the set boundary. The control unit 1800 may calculate a current location based on received location information, and may control the traveling unit 1300 so that the calculated current location is located within the travel area set by the boundary.

In addition, the control unit 1800 may determine obstacle information input by the obstacle detector 1402 and travel avoiding obstacles. Also, the control unit 1800 may modify a preset travel area, if necessary, based on the obstacle information.

For example, the control unit 1800 may control the traveling unit 1300 to travel by passing through an obstacle or avoiding the obstacle, by way of changing a moving direction or a travel path in correspondence with obstacle information input from the obstacle detector.

The control unit 1800 may set the moving robot so as not to approach a cliff by a predetermined distance or closer when the cliff is detected. In addition, the control unit 1800 may change a traveling direction according to a user selection, which may be input through the terminal 200, by way of transmitting traveling information regarding a detected obstacle to the terminal 200 and displaying such information on the terminal.

The power supply unit 1900 may include a rechargeable battery (or battery module) (not shown). The battery may be detachably mounted to the moving robot 100. When it is detected through the sensing unit 1400 that the battery gauge is insufficient, the control unit 1800 may control the traveling unit 1300 to move the moving robot to the location of a charging station for recharging the battery. When presence of the charging station is detected by the sensing unit 1400, recharging of the battery may be performed.

Hereinafter, the main configuration of the terminal 200 that performs communication with the moving robot 100 according to the present disclosure will be described, with reference to FIG. 2C.

Referring to FIG. 2C, the terminal 200 may include a mobile terminal that can be carried by a user and may include a communication unit 210, an input unit 220, a UWB module 230, a location detecting unit 240, a display unit 251, a memory 260, and a control unit 280.

The communication unit 210 may perform communication with an external server or the moving robot 100 through wireless communication. The communication unit 210 may transmit and receive data by being equipped with a communication module such as Wi-Fi, WiBro, and the like, as well as through short-range wireless communications such as Zigbee and Bluetooth. In addition, the communication unit 210 may include a UWB module for transmitting a UWB signal.

The input unit 220 may include an input element such as at least one button, a switch, or a touch pad.

The display unit 251 may include a touch sensor to receive a control command through a touch input. In addition, the display unit 251 may be configured to output a control screen for controlling the moving robot 100, and a map screen on which a set boundary and the location of the moving robot 100 may be displayed.

The memory 260 may store therein data related to the travel of the moving robot 100. In addition, the memory 260 may store therein location information regarding the moving robot 100 and the terminal 200, and information regarding a travel area of the moving robot and a boundary of the travel area. For example, the memory 1600 may store data that is readable by a microprocessor, and may be one of a hard disk drive (HDD), a solid state disk (SSD), a silicon disk drive (SDD), ROM, RAM, CD-ROM, a magnetic tape, a floppy disk, or an optical data storage device.

The position detector 240 may include a plurality of sensor modules for transmitting and receiving location information. For example, the location detecting unit 240 may include a GPS module, an Ultra-Wideband (UWB) module, a geomagnetic sensor, an acceleration sensor, a gyro sensor, and the like, to recognize coordinates of a point which is indicated by a posture change such as a tilt or the like, as well as a current location of the terminal 200.

The UWB module 230 which may be included in the location detecting unit 240 or separately provided may exchange UWB signals with the moving robot 100 and/or the location information transmitter 50. Accordingly, not only the location of the terminal 200 but also the location of the moving robot 100 with respect to the terminal 200, the location of the location information transmitter 50 with respect to the terminal 200, the location of the location information transmitter 50 with respect to the moving robot 100, and the like can be recognized.

The UWB module 230 may transmit or receive a UWB signal through a UWB module provided in the moving robot 100. The terminal 200 may play a role of 'remote control device' in that the terminal 200 can control the travel or weeding operation of the moving robot 100 through communication with the moving robot 100.

In addition to the UWB module 210, the terminal 200 may further include a gyro sensor and a distance measuring sensor.

The gyro sensor may detect a change in a three-axis value according to the movement of the terminal 200. Specifically, the gyro sensor may detect an angular velocity according to the movement of the terminal 200 by which at least one of x, y or z-axis values is changed.

Also, the gyro sensor may use x, y, and z axis values, which are detected at a specific time point, as a reference point, and detect x', y', and z' axis values that change with respect to the reference point after reception of a predetermined input and/or a lapse of a predetermined period of time. To this end, the terminal 200 may further include a magnetic sensor (not shown) and an acceleration sensor (not shown) as well as the gyro sensor.

The distance measuring sensor may emit at least one of a laser light signal, an IR signal, an ultrasonic signal, a carrier frequency, or an impulse signal, and may calculate a distance from the terminal 200 to the corresponding signal based on a reflected signal.

To this end, the distance measuring sensor may include, for example, a time of flight (ToF) sensor. For example, the ToF sensor may include a transmitter that emits an optical signal transformed to a specific frequency, and a receiver that receives and measures a reflected signal. When the ToF sensor is installed on the terminal 200, the transmitter and the receiver may be spaced apart from each other to avoid signal affection therebetween.

Hereinafter, the laser light signal, the IR signal, the ultrasonic signal, the carrier frequency, the impulse signal, and/or the UWB signal described above may collectively be referred to as 'signal'. In this specification, 'UWB signal' which is rarely affected by an obstacle will be exemplarily described. Therefore, it can be said that the distance measuring sensor plays a role of calculating a distance from the terminal 200 to a point where a signal is emitted. In addition, the distance measuring sensor may include a transmitter that emits signals and one receiver or a plurality of receivers for receiving reflected signals.

Figure 3:
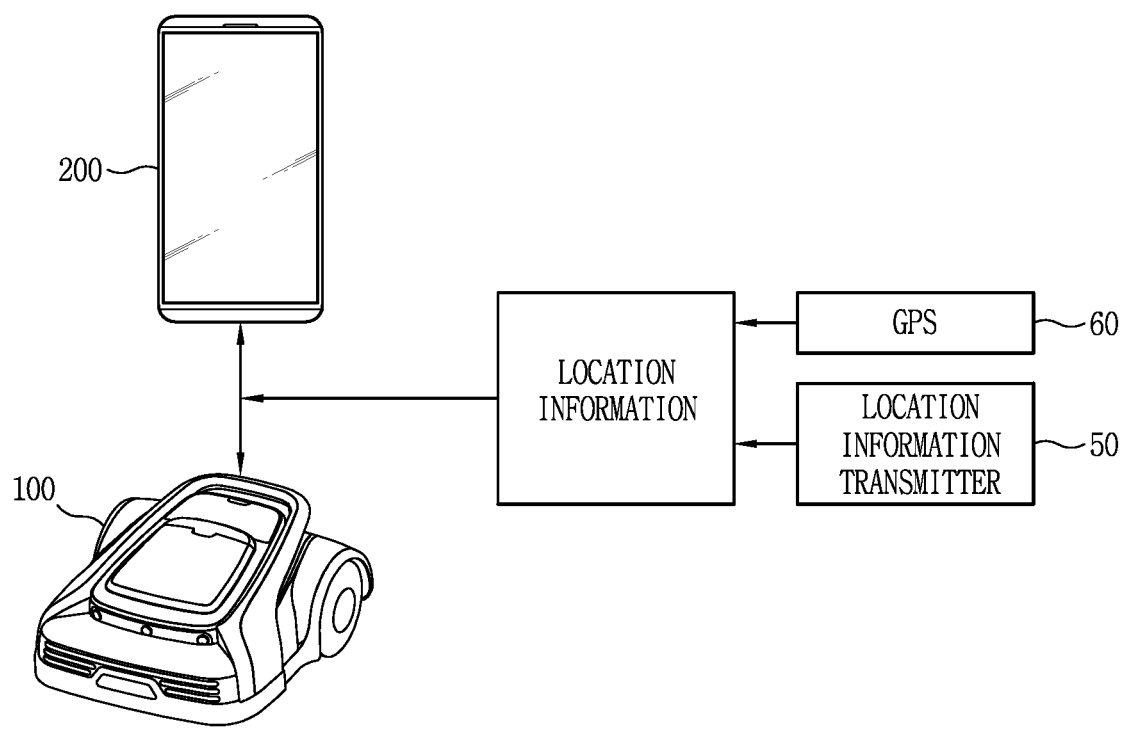
FIG. 3 is a conceptual view illustrating a signal flow between devices for setting a boundary for the moving robot, in accordance with an embodiment of the present disclosure.

Hereinafter, FIG. 3 is a conceptual view illustrating a signal flow of devices for setting a boundary with respect to a moving robot, for example, a signal flow of the moving robot 100, the terminal 200, a GPS 60, and the location information transmitter 50.

When the location information transmitter 50 transmits a signal by its UWB sensor, the terminal 200 may receive a signal related to location information from the location information transmitter 50 through a UWB module provided in the terminal 200 itself. At this time, a signaling method of the location information transmitter 50 and a signaling method between the moving robot 100 and the terminal 200 may be the same or different from each other.

For example, the terminal 200 may transmit ultrasonic waves and the moving robot 100 may receive the ultrasonic waves of the terminal 200 to follow the terminal 200. As another example, a marker may be attached on the terminal 200. The moving robot 100 may recognize the marker attached on the terminal 200 by capturing a moving direction of the terminal, so as to follow the terminal 200.

In FIG. 3, location information may be received from the location information transmitter 50 or the GPS 60. A GPS signal, an ultrasonic signal, an infrared signal, an electromagnetic signal, or a UWB signal may be used as a signal corresponding to the location information.

The moving robot may need to collect location information for setting a travel area and a boundary. The moving robot 100 may collect location information by setting any one point of an area as a reference location. At this time, a location of any one of an initial starting point, the charging station, and the location information transmitter 50 may be set as the reference location. The moving robot 100 may generate coordinates and a map for the area on the basis of the set reference location and store the generated coordinates and the map. When the map is generated and stored, the moving robot 100 may move based on the map.

In addition, the moving robot 100 may set a new reference location at every operation, and determine a location within the area based on the newly-set reference location.

Also, the moving robot 100 may receive location information collected from the terminal 200 which is moving along a predetermined path. The terminal 200 may move arbitrarily and its moving path may change according to a subject which moves (carries) the terminal. However, in order to set a travel area of the moving robot, the terminal 200 may preferably move along an outer side of the travel area.

The terminal 200 may calculate coordinates of a location in an area based on a reference location. In addition, the moving robot 100 may collect location information while moving with and following the terminal 200.

When the terminal 200 or the moving robot 100 travels along a predetermined path alone, the terminal 200 or the moving robot 100 may calculate a current location based on a signal transmitted from the GPS 60 or the location information transmitter 50.

The moving robot 100 and the terminal 200 may move by setting the same reference location with respect to a predetermined area. When the reference location is changed at every operation, the reference location set with respect to the terminal 200 and location information collected from the reference location may be transmitted to the moving robot 100. The moving robot 100 may set a boundary based on the received location information.

Meanwhile, the moving robot 100 and the terminal 200 may determine their relative locations using Ultra-wide Band (UWB) technology. To this end, one of UWB modules may be a UWB anchor and the other one may be a UWB tag.

For example, the UWB module 230 of the terminal 200 may operate as 'UWB tag' that emits a UWB signal, and the UWB module of the moving robot 100 may operates as 'UWB anchor' that receives a UWB signal.

However, it should be noted that the present disclosure is not limited to this. For example, the UWB module 230 of the terminal 200 may operate as a UWB anchor, and the UWB module of the moving robot 100 may operate as a UWB tag. In addition, the UWB module may include one UWB anchor and a plurality of UWB tags.

Hereinafter, description will be given of a method in which the moving robot 100 and the terminal 200 determine (recognize) their relative positions through a UWB communication technology. First, a distance between the moving robot 100 and the terminal 200 may be calculated using a distance measurement technology such as a ToF (Time of Flight) scheme.

Specifically, a first impulse signal, which is a UWB signal radiated (emitted) from the terminal 200, may be transmitted to the moving robot 100. To this end, the UWB module of the terminal 200 may operate as 'UWB tag' for transmission and the UWB module of the moving robot 100 may operate as 'UWB anchor' for reception.

Here, the UWB signal (or the impulse signal) can be smoothly transmitted and received even if an obstacle exists in a specific space, and the specific space may have a radius of several tens of meters (m).

The first impulse signal may be received through the UWB anchor of the moving robot 100. The moving robot 100 which has received the first impulse signal may transmit a response signal to the terminal 200. Then, the terminal 200 may transmit a second impulse signal, which may be a UWB signal with respect to the response signal, to the moving robot 100. Here, the second impulse signal may include delay time information which may be calculated based on a time at which the response signal has been received and a time at which the second impulse signal has been transmitted responsive to the response signal.

The control unit of the moving robot 100 may calculate a distance between the moving robot 100 and the terminal 200, based on a time at which the response signal has been transmitted, a time at which the second impulse signal has been arrived at the UWB anchor of the moving robot 100, and the delay time information included in the second impulse signal.

$$\text{Distance} = c \times \frac{t_2 - t_1 - treply}{2}$$

Here, $t_2$ denotes an arrival time of the second impulse signal, $t_1$ denotes a transmission time of the response signal, treply denotes a delay time, and c denotes a constant value indicating a speed of light.

As such, the distance between the moving robot 100 and the terminal 200 can be determined by measuring a time difference between signals transmitted and received between the UWB tag and the UWB anchor included in the moving robot 100 and the terminal 200, respectively.

A distance between the moving robot 100 and the location information transmitter 50 and a distance between the terminal 200 and the location information transmitter 50 can also be determined in the same or similar manner.

Hereinafter, an operation of setting a boundary with respect to the moving robot 100 using the location information transmitter 50 and the terminal 200 without laying wires under the ground will be described, with reference to FIGS. 4A to 4C.

In this manner, a boundary which is a reference of a travel area may be set using the location information transmitter 50, the terminal 200, and the moving robot 100, or using only the location information transmitter 50 and the moving robot 100, without embedding wires. A travel area which is distinguished by the boundary may be referred as to 'wireless area.'

The 'wireless area' may be one or plural. In addition, one wireless area may include a plurality of spot areas additionally set in the corresponding area, so that a mowing function performed by the moving robot 100 can be performed more efficiently.

A boundary must be set so that the moving robot 100 can perform mowing while moving in a travel area set outdoors. Then, a travel area, namely, a wireless area in which the moving robot 100 is to travel may be designated inside the set boundary.

Figure 4A:
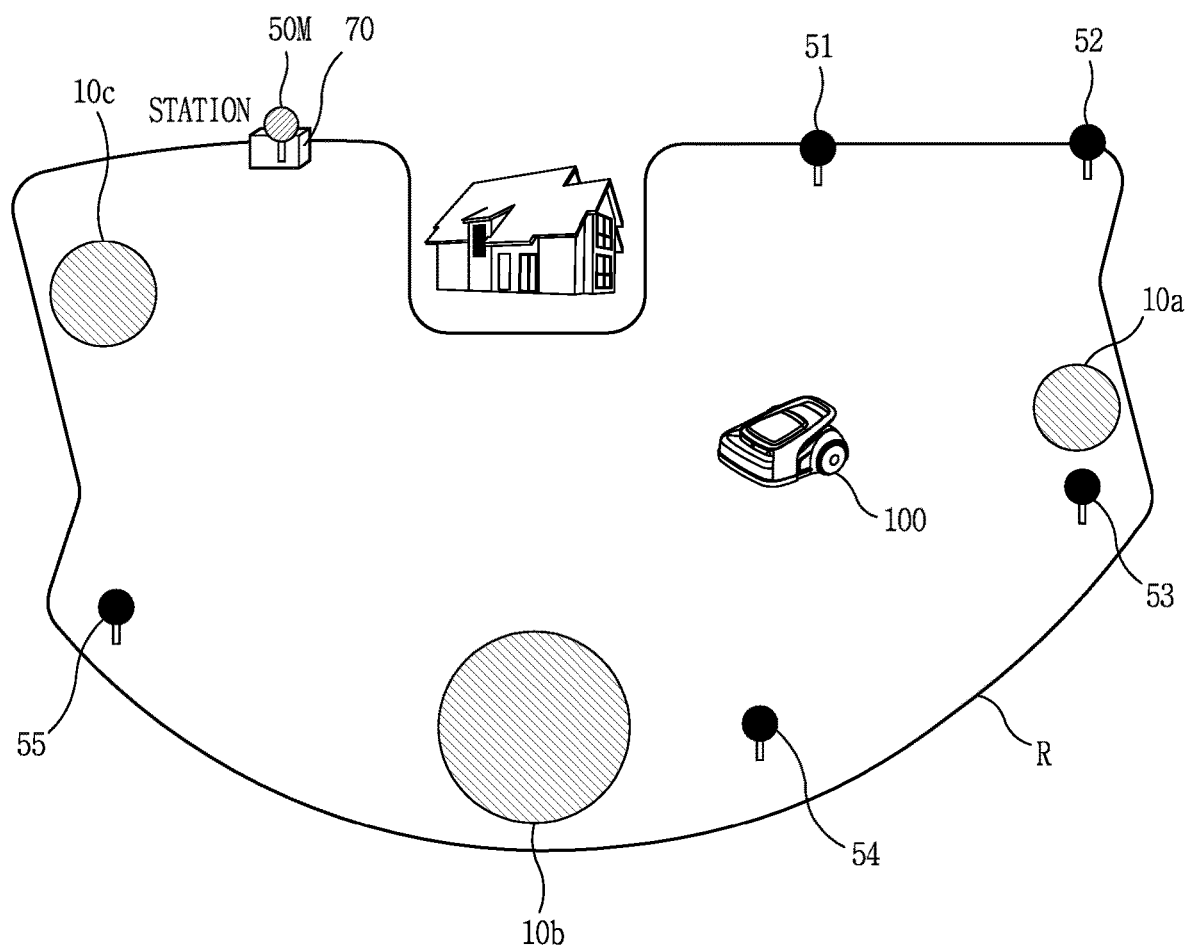
FIG. 4A is a conceptual view related to setting a virtual boundary for the moving robot without laying wires under the ground, in accordance with an embodiment of the present disclosure.

Referring to FIG. 4A, there may be various obstacles 10a, 10b, and 10c at the outdoors in addition to a house illustrated in the drawing. Here, the obstacles 10a, 10b, and 10c may include, for example, fixed obstacles such as a building, a rock, a tree, a swimming pool, a pond, a statue, a garden, and the like, which exist at the outdoors, and obstacles that move. Also, size and shape of the obstacles 10a, 10b, and 10c may vary.

If the obstacles are present close to a set boundary, the boundary must be set, from the beginning, to avoid these various obstacles 10a, 10b, 10c.

However, as illustrated in FIG. 4A, when the obstacles 10a, 10b, and 10c exist within a travel area set based on a boundary R, additional boundaries for the respective obstacles 10a, 10b, and 10c should be set or the previously-set boundary should be changed through the same or similar process to the method of setting the travel area inside the boundary R.

Also, in the present disclosure, a plurality of location information transmitters 50M, 51, 52, 53, 54, and 55 may be installed in advance in a predetermined area, in order to set a boundary without laying wires.

The plurality of location information transmitters 50M, 51, 52, 53, 54, and 55 may transmit signals. Specifically, the plurality of location information transmitters 50M, 51, 52, 53, 54, and 55 may transmit signals to one another or may transmit signals to the moving robot 100 and/or the terminal 200.

Here, the signals may include, for example, UWB signals, ultrasonic signals, infrared signals, Bluetooth signals, Zigbee signals, or the like.

At least three of the plurality of location information transmitters 50M, 51, 52, 53, 54, and 55 may be installed in a spaced manner. Also, the plurality of location information transmitters 50M, 51, 52, 53, 54, and 55 may be installed at high points higher than a reference height, in order to minimize signal interference when the UWB sensor is not included.

The plurality of location information transmitters 50M, 51, 52, 53, 54, and 55 may be installed at locations adjacent to a boundary to be set. The plurality of location information transmitters 50M, 51, 52, 53, 54, and 55 may be installed outside or inside a boundary to be set.

For example, FIG. 4A illustrates a plurality of location information transmitters 50M, 51, 52, 53, 54, and 55 installed inside the boundary R, but the present disclosure is not limited thereto. For example, the plurality of location information transmitters 50M, 51, 52, 53, 54 and 55 may be installed outside the boundary R, or some may be installed inside the boundary R and the others outside the boundary R.

When the location information transmitter 50M, 51, 52, 53, 54, 55 includes a UWB sensor, the UWB sensor may transmit and receive UWB signals to and from the moving robot 100 and/or the terminal 200 located in a predetermined area, so as to calculate location information regarding the moving robot 100 and/or the terminal 200.

For example, the moving robot 100 may calculate the location of the moving robot 100 by comparing amounts/intensities of signals of the plurality of location information transmitters 50M, 51, 52, 53, 54, and 55 and determining a spaced distance and direction from each location information transmitter. A method of calculating location information regarding the terminal 200 may be similarly performed.

At least one of the plurality of location information transmitters 50M, 51, 52, 53, 54, and 55 may be a reference location information transmitter 50M for setting a boundary. The reference location information transmitter 50M may be installed at a place where a charging station 70 is located, for example, as illustrated in FIG. 4A.

Coordinate values of the plurality of location information transmitters 50M, 51, 52, 53, 54, and 55 may be set based on the reference location information transmitter 50M. More specifically, the location information transmitter 50M may transmit and receive signals to and from the remaining location information transmitters 51, 52, 53, 54, and 55, to calculate x and y coordinate values corresponding to the locations of the remaining location information transmitters, with respect to the reference location information transmitter as a zero point. Accordingly, the location information regarding the plurality of location information transmitters 50M, 51, 52, 53, 54, and 55 can be set.

When the moving robot 100 sets the charging station 70 where the reference location information transmitter 50M is located as an operation start point, it may be easier to determine (recognize) the location of the moving robot 100 at every operation. Also, when a battery gauge is insufficient during the travel of the moving robot 100, the moving robot 100 may move to the reference location information transmitter 50M where the charging station 70 is located and charge the battery.

When the reference location information transmitter 50M is installed at a place where the charging station 70 is located, it may not be necessary to set the location of the charging station 70 separately.

On the other hand, when the moving robot 100 becomes significantly far away from the reference location information transmitter 50M as it keeps traveling, the reference location information transmitter may be changed to another location information transmitter which may be located close to a current location of the moving robot, based on amounts/intensities of signals transmitted from the plurality of location information transmitters 50M, 51, 52, 53, 54, and 55.

On the other hand, unlike FIG. 4A, when the charging station 70 is located outside the boundary R, that is, when the boundary has been set at an inner side than the charging station 70, the moving robot 100 may return to the charging station over the boundary for recharging the battery.

However, when the charging station 70 is located outside the boundary, a moving area (not shown) may be additionally set between the charging station 70 and the travel area set within the boundary, so as to guide the moving robot 100 to return to the charging station 70 located outside the boundary.

Figure 4B:
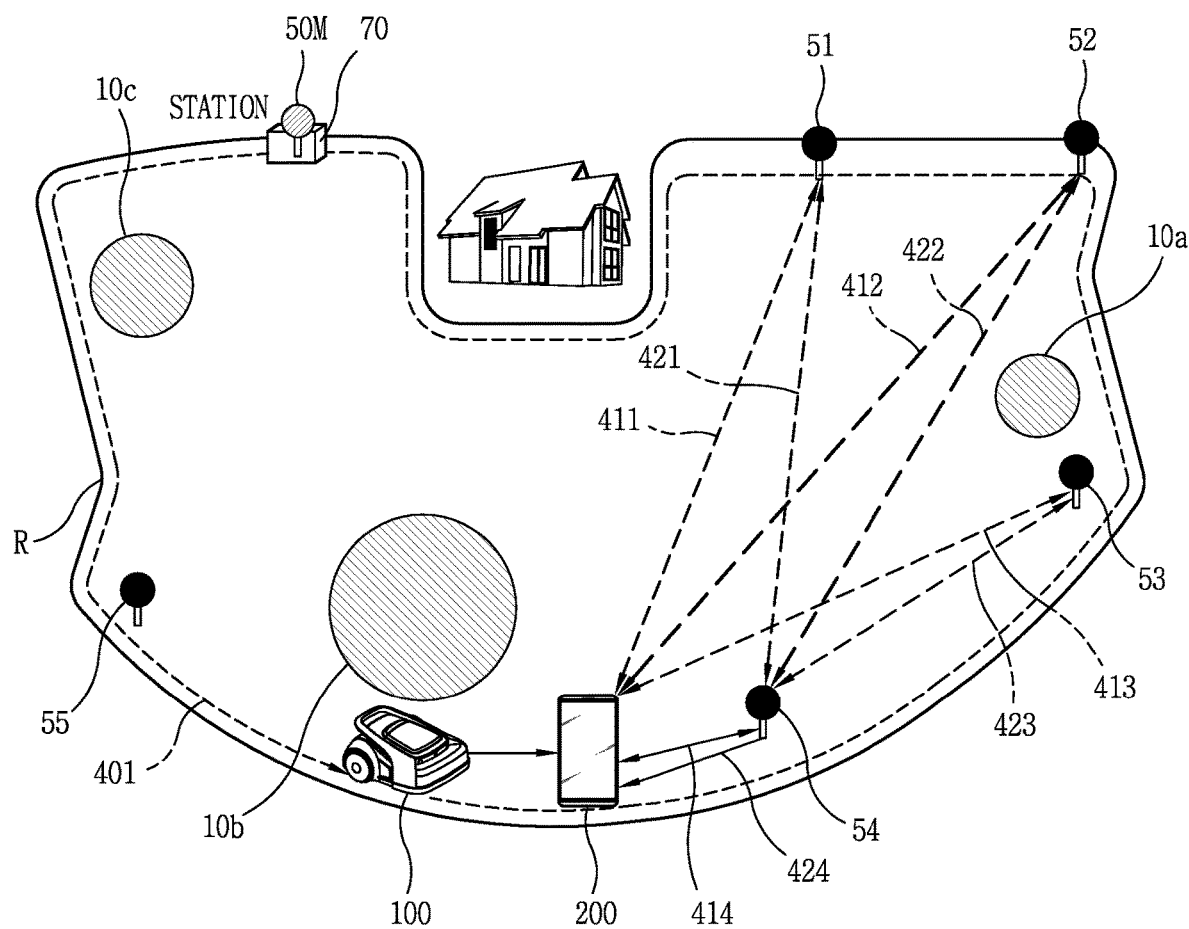
FIG. 4B is another conceptual view of FIG. 4A, in accordance with an embodiment of the present disclosure.

Hereinafter, FIG. 4B illustrates an exemplary method of setting a boundary for the moving robot 100 and a travel area with respect to the boundary, by using the plurality of location information transmitters 50M, 51, 52, 53, 54, and 55 and the terminal 200.

First, the terminal 200 may move from the location information transmitter 55 along a first path 401 at an outside of an area, in which lawn is planted. At this time, the terminal 200 may be moved by a person, but may also be moved by another transportation device such as a drone.

The terminal 200 may determine a current location through the location information transmitter 55 or a GPS. As the mobile terminal 200 moves, a distance and direction to each location information transmitter may be calculated based on signals transmitted from the other location information transmitters 51 to 54. Accordingly, coordinates of a plurality of points corresponding to the change of the location of the terminal 200 may be recognized and stored as location information.

In this regard, each of the plurality of location information transmitters 50M, 51, 52, 53, 54, and 55 may transmit a UWB signal including unique information for identifying the signal. Accordingly, the terminal 200 can individually analyze and process a first signal 411 transmitted from the first location information transmitter 51, a second signal 412 transmitted from the second location information transmitter 52, a third signal 413 transmitted from the third location information transmitter 53, and a fourth signal 414 transmitted from the fourth location information transmitter 54.

In addition to this, the first to third location information transmitters 51 to 53 may transmit and receive signals 421 to 423 to the fourth location information transmitter 54, which may be located close to the current location of the terminal 200, receive a response signal to the transmitted signals, and transmit a signal 424 corresponding to the response signal to the terminal 200. The terminal can check whether or not there is an error between the current location of the corresponding location information transmitter 54 and a predefined location (initially-installed point) based on the signal 424.

According to this, the location error of the location information transmitter can be checked together when the moving robot 100 moves for setting the travel area or the wireless area.

When the movement corresponding to the first path 401 is completed, for example, when the first path 401 forms a shape of a closed curve or reaches a designated end point, the terminal 200 may transmit location information, which has been stored while moving along the first path 401, to the moving robot 100.

Then, the moving robot 100 may set a line, which sequentially connects the location information stored while the terminal 200 moves along the first path 401, or an outer line of the line, as a boundary R. In addition, the moving robot 100 may set an inner area of the first path 401 with respect to the set boundary R as a travel area or a wireless area.

The moving robot 100 may perform test traveling in the set travel area or wireless area. At this time, the boundary and/or the travel area may be partially modified by the moving robot 100. For example, the boundary and/or the travel area for the moving robot 100 may be partially modified in consideration of situation information, collected when a new obstacle is detected, when an existing obstacle is removed, when an uneven surface or a pothole is detected, or when a non-travelable spot due to the traveling function of the moving robot 100 is detected.

Or, as illustrated in FIG. 4B, the moving robot 100 may follow the location of the terminal 200 at a predetermined distance while the terminal 200 moves along the first path 401, and accordingly the boundary and/or the travel area for the moving robot 100 can be set without additional test traveling.

At this time, there may be a difference between the first path 401 along which the terminal 200 has moved and the moving path of the moving robot 100 following the terminal 200. That is, the moving robot 100 can move, following the terminal 200, while ignoring or removing a location which the moving robot 100 cannot follow on the track of the first path 401, along which the terminal 200 has moved. In this case, the moving robot 100 may store the corresponding location change and may keep following the current location of the terminal 200 based on points corresponding to the location change.

When the distance between the terminal 200 and the moving robot 100 exceeds a predetermined distance as the traveling speed of the moving robot 100 is slowed due to obstacle avoidance or the like, a designated warning sound ('first warning sound') may be output from the moving robot 100 to notify the excess so that a user or the like moving the terminal 200 can stop the movement of the terminal 200.

Thereafter, when the moving robot 100 restarts to travel by avoiding obstacles and the like in a designated manner and accordingly the distance to the terminal 200 in the stopped state is reduced to be in a designated range again, a corresponding warning sound ('second warning sound') may be output from the moving robot 100 to notify it so that the user or the like moving the terminal 200 can perform the movement.

Meanwhile, FIG. 4B, for example, illustrates that the location information regarding the moving robot 100 and/or the terminal 200 may be calculated by the plurality of location information transmitters 50M, 51, 52, 53, 54, and 55 upon movement for setting the travel area or wireless area, but such location information may, of course, be calculated through GPS.

Figure 4C:
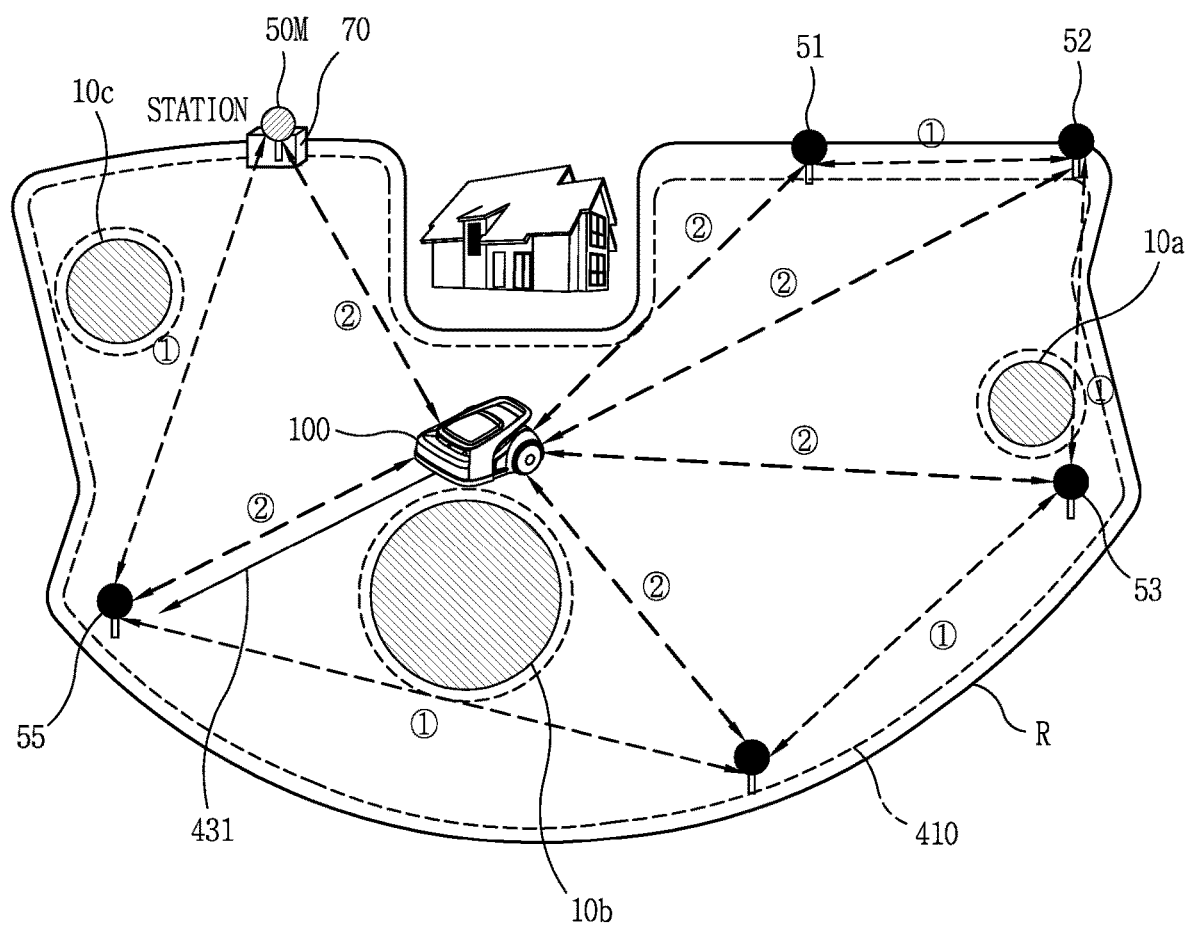
FIG. 4C is another conceptual view of FIG. 4A, in accordance with an embodiment of the present disclosure.

FIG. 4C, for example, illustrates that additional boundaries for a plurality of obstacles 10a, 10b, and 10c existing in a travel area (or wireless area) 410 in a state where a boundary R and the travel area inside the boundary R may be set.

In FIG. 4C, if there are obstacles 10a, 10b, and 10c having a predetermined size or greater inside the set travel area 410, additional boundaries for the detected obstacles 10a, 10b, and 10c may be set.

The moving robot 100 (or the terminal 200 and the moving robot 100 or the terminal 200) may set additional boundaries and a travel area with respect to the additional boundaries by moving along outer peripheries of the obstacles 10a, 10b, and 10c in the same or similar manner as described above with reference to FIG. 4B.

In FIG. 4C, dashed lines formed at the outside of the obstacles 10a, 10b, 10c may indicate the additional boundaries. Unlike the boundary set in FIG. 4B, an inner side may be set as a non-travelable area and an outer side may be set as a travelable area, with respect to the set additional boundary.

Thus, the change of the travel area due to the setting of the additional boundary can be reflected in the modification of the existing boundary and travel area. A map corresponding to the existing boundary and travel area can also be modified accordingly.

The moving robot 100 may perform operations such as weeding and the like while moving in the travelable area within the travel area. While the moving robot 100 moves in the travelable area within the travel area, the plurality of location information transmitters 50M, 51, 52, 53, 54 and 55 may transmit signals, for example, UWB signals ①  to one another, thereby determining their locations. Also, the plurality of location information transmitters 50M, 51, 52, 53, 54 and 55 may transmit signals, for example, UWB signals ② to the moving robot 100, so that the moving robot 100 can recognize its current location within the travel area.

On the other hand, in the case of fixed obstacles having a predetermined size or greater existing in the travel area, the setting of the additional boundaries and the change of the travel area may be carried out for smooth travel of the moving robot 100 although time and effort may be required. Further, since moving obstacles change in position every time, the moving robot 100 can sufficiently travel while avoiding the moving obstacles through its sensors.

However, temporary obstacles which are installed for a predetermined period of time may be removed after the lapse of the corresponding period of time. Therefore, the temporary obstacles may need to be treated differently from the fixed obstacles and the moving obstacles. Examples of such temporary obstacles may include a barbecue facility, a simple swimming pool, event installations and the like that are installed only during specific seasons.

Specifically, in the case where the temporary obstacle is registered as the fixed obstacle, when the temporary obstacle is removed, not only may the additional boundary setting and the travel area change for the registration but also re-changing tasks of the boundary and travel area due to the removal may be performed. Also, in the case where the temporary obstacle is treated equally as the moving obstacle, even though the temporary obstacle is fixed at the same location for a predetermined period of time, the moving robot 100 may repeatedly design obstacle avoidance to be the same as the initial design, which interferes with smooth travel of the moving robot 100.

On the other hand, there may be a need to set a predetermined area, which is not a material object such as the temporary obstacle, as a non-travelable area for a predetermined period of time to avoid it during travel. For example, the predetermined area may be a spot area in which grass is not to be cut temporarily or a point where a slip occurs temporarily. Even in such a case, it may be better to deal with it as in the case of temporary obstacles.

In the following description, the temporary obstacle and an object/location area desired to be set as a temporary non-travelable area are all defined as 'target.'

When a target is an object having a predetermined size, namely, a temporary obstacle, a location of the target may include a plurality of coordinates. Also, a location area desired to be set as a temporary non-travelable area may include a plurality of coordinates. In such a case, one of the plurality of coordinates may represent the location of the target. That is, 'target point' may refer to any one of a plurality of coordinates occupied by the target. In addition, the 'target point' may refer to the location of the target.

The present disclosure may implement a method of registering 'target' on a map corresponding to a set boundary and a set travel area and, in particular, registering and removing 'target' more quickly than a fixed obstacle.

Hereinafter, a method of controlling the moving robot 100 according to an embodiment of the present disclosure will be described in detail, with reference to FIG. 5.

Referring to FIG. 5, the moving robot 100 may set a virtual boundary and a travel area on the basis of the boundary without laying wires (S10).

Specifically, the moving robot 100 may set a virtual boundary on the basis of location information based on signals, for example, UWB signals, received from a plurality of location information transmitters provided in a predetermined area, and set a travel area with respect to the boundary.

In order to set the boundary and the travel area, when the location change in response to the unique movement of the terminal 200 is recognized based on signals received from GPS or the plurality of location information transmitters and then points corresponding to a plurality of locations are transmitted to the moving robot 100, the moving robot 100 may set a virtual boundary by sequentially connecting the plurality of points and set a travel area inside the boundary. Thereafter, the moving robot 100 may perform test traveling in the set travel area and change the set boundary and travel area.

Alternatively, the moving robot 100 may set a virtual boundary and a travel area with avoiding obstacles and the like, while following the terminal 200 along a moving path of the terminal at a predetermined distance from the terminal.

On the other hand, a fixed obstacle existing inside the set travel area may be detected and registered on the same or similar manner as the setting of the boundary and the travel area described above.

For example, the terminal 200 may generate a path while moving outside the fixed obstacle. The moving robot 100 may then perform test traveling along the generated path and modify the preset boundary and travel area. Accordingly, the fixed obstacle may be registered.

Alternatively, for example, the terminal 200 may move outside the fixed obstacle. The moving robot 100 may set a travelable area and a non-travelable area with respect to a path, which is generated as the moving robot 100 keeps track of the location corresponding to the movement of the terminal. Accordingly, the fixed obstacle may be registered.

Next, in order to register a target on a map, the moving robot 100 may recognize the location of the terminal 200 and receive location information regarding a target point pointed by the terminal at the recognized location of the terminal 200 (S20).

Here, the location of the terminal 200 may be recognized based on a signal transmitted through GPS or a location information transmitter 50 installed close to the boundary. For example, the terminal 200 having a UWB sensor may transmit the UWB signal to the neighboring location information transmitters 50, and calculate a distance and direction based on amounts/intensities of UWB signals received from the neighboring location information transmitters 50, thereby recognizing a current position of the terminal 200. The terminal 200 may be located within the boundary, or outside the boundary.

Next, the terminal 200 may point to a spot where a target such as a temporary obstacle exists. The spot pointed by the terminal 200 may be referred to as 'target point.' Specifically, the target point may refer to single coordinates pointed by the terminal 200, among a plurality of coordinates points that match targets, for example, temporary obstacles, which are to be set as non-travelable areas within the travel area of the moving robot.

Hereinafter, a detailed process of pointing a target and calculating a location of the pointed target will be described.

Specifically, a user who grips the terminal 200 may tilt the terminal 200 toward a point where a target exists within the boundary, without moving the terminal 200 at the current location.

To this end, the terminal 200 should be able to detect a spatial motion variation at the current location. In order to detect the spatial motion variation, the terminal 200 may include at least one of a six-axis acceleration sensor, an Inertial Measurement Unit (IMU) sensor, and a six-axis gyro sensor.

The acceleration sensor is a sensor that measures how much force an object is receiving based on gravitational acceleration of the earth. A three-axis acceleration sensor refers to a sensor capable of measuring magnitude of acceleration in x, y, and z-axial directions. Such an acceleration sensor may be used as one three-axis acceleration sensor, a six-axis acceleration sensor with two three-axis acceleration sensors applied, or a nine-axis acceleration sensor with three three-axis acceleration sensors applied.

By using a sensing value of the three-axis acceleration sensor, roll (rotation with respect to the x axis) and pitch (rotation with respect to the y axis) may be calculated. A unit used is [g]. On the other hand, rotation with respect to the z axis coinciding with the direction of gravitational acceleration, that is, a yaw (rotation with respect to the z axis) value may be calculated only by additionally applying a three-axis gyro sensor or a magnetometer. Also, in a motion state in which an object is not stopped, a tilt value cannot be detected by only the three-axis acceleration sensor.

The three-axis gyro sensor is a sensor for controlling posture of an object, namely, a sensor capable of measuring angular velocity in the x, y, and z-axial directions. Here, the angular velocity refers to an angle of rotation per hour. A unit used is [degree/sec].

The IMU sensor is a combined sensor of a three-axis acceleration sensor and a three-axis gyro sensor. Alternatively, the IMU sensor is a nine-axis sensor with a three-axis acceleration sensor, a three-axis gyro sensor, and a three-axis geomagnetic sensor. By using such an IMU sensor, the roll, the pitch and the yaw can all be calculated.

In the present disclosure, a three-axis or six-axis gyro sensor and a three-axis or six-axis acceleration sensor may be built in, or an IMU sensor may be installed in the terminal 200 so that speed variation in the three axis directions of the terminal 200 can all be detected.

Since the terminal 200 does not move at the current location, value variation may not occur or may be negligible in the x and y axes, and may occur only in the z axis.

Since x and y coordinate values corresponding to the current location of the terminal 200 can be obtained based on the UWB signals transmitted from the neighboring location information transmitters 50, a point where the z axis becomes '0' at the current location, namely, a bottom point may be set to 'zero (0) point.'

Subsequently, when the terminal 200 points to a spot (point) where the target exists within the boundary, the terminal 200 accordingly may detect a posture change and simultaneously transmit a signal to the spot.

Here, the pointing may be defined as an operation of tilting the main body of the terminal 200 toward the point where the target exists within the boundary and maintaining the tilted state for a predetermined time.

In this case, a trigger operation before pointing or a completion operation after pointing may be added to determine a time point of the pointing. The trigger operation or completion operation, for example, may include all of a voice command, a touch input applied on a touch screen of the terminal 200, a preset touch gesture, a push input/forced touch input applied on one area of the main body of the terminal 200, and the like.

Here, the signal may include a UWB signal, an IR signal, a laser signal, a ZigBee signal, or the like. When the terminal 200 transmits the UWB signal, a problem that signal reception is interrupted may be solved even if an obstacle exists between the terminal 200 and the target. Therefore, even when the terminal 200 is located far from the target within the boundary, signal transmission corresponding to the pointing can be performed.

When the signal is transmitted from the terminal 200 to the target point, the terminal 200 may sense a value variation in the z axis with respect to 'zero point' through of the gyro sensor and the acceleration sensor, or through the IMU sensor.

Then, a transmission distance of the signal corresponding to the pointing may be calculated, to calculate the x, y, and z coordinates values of the point where the target exists, namely, the target point. Here, if the target point is defined as a bottom point, since the z coordinates value is defined as '0', only the x and y coordinates values can be actually calculated.

Meanwhile, the value variations of the gyro sensor and the acceleration sensor or the IMU sensor corresponding to the posture change of the terminal 200 may be displayed on the display unit 151 of the terminal 200, to facilitate checking whether or not the terminal 200 has correctly pointed to the point where the target exists. Or, appropriate guide information may be displayed on the display unit 151 of the terminal 200.

Or, when the map corresponding to the boundary and the travel area for the moving robot 100 is stored in the terminal 200, the stored map may be output on the display unit 151 of the terminal 200 and the target point pointed by the terminal 200 may be displayed on the output map.

In this manner, when the location information regarding the target point pointed by the terminal 200 is calculated, the moving robot 100 can receive the calculated location information from the terminal 200.

Then, the moving robot 100 may store the received location information in a memory or the like (S30).

The moving robot 100 may reflect the location information regarding the target point to the preset boundary and travel area. For example, a specific area (surrounding area) including coordinates of a target point which matches the stored location information on a map stored in the memory of the moving robot 100 may be set as a non-travelable area.

Here, the specific area may be an area having a predetermined size centered on the coordinates of the target point. For example, the specific area may be set as an area having a designated length/width size centered on the target point. In addition, the specific area may be set as an area having a designated radius from the target point.

The specific area may also be an area having a designated size having the coordinates of the target point as one vertex. In this case, it may be requested to input a coordinate value of an additional vertex for connecting with the coordinates of the target point.

The specific area may also correspond to the coordinates of the target point, in some cases.

Also, the terminal 200 may reflect the location of the target point directly to the map for the moving robot 100, stored in its own memory.

Alternatively, when communication with the moving robot 100 is enabled in response to an execution of an application for controlling the moving robot, the terminal 200 may transmit the location information related to the target point to the moving robot 100 or register the location information related to the target point in a linked server.

As such, when the location information regarding the target point calculated by the terminal 200 is recognized by the moving robot 100 (through reception and storage), when the location information regarding the target point is registered on the map stored in the terminal 200, or when the location information regarding the target point is registered on the map through the linked server or the like, it may be expressed as 'The target has been registered' or 'Registration of target'. Or, it may be expressed as 'Registration of temporary obstacle'.

While the location of the 'target' is calculated as described above, the moving robot 100 can be located anywhere within the boundary.

In other words, unlike the initial boundary setting and the travel area setting, or the additional boundary setting and the travel area change for registration of the fixed obstacle, the moving robot 100 may not have to move along an outer periphery of the target. That is, by registering the target quickly using only the terminal 200, both user convenience and smooth travel of the moving robot 100 can all be achieved. In addition, since the moving robot 100 can continue to perform its original function while the target is registered, it may be advantageous in terms of time and efficiency.

After the registration of the target is completed, when a predetermined area including coordinates that match the stored location information is recognized while moving in the travel area, the moving robot 100 may move while avoiding the recognized predetermined area (S40).

Here, the coordinates that match the stored location information may refer to a point corresponding to the x and y coordinates that match the location information regarding the target point. Accordingly, the predetermined area including the coordinates matched with the stored location information may refer to an area including the point corresponding to the x and y coordinates.

The moving robot 100 may travel a travelable area and a non-travelable area within the travel area in a distinguishing manner based on the predetermined area including the coordinates that match the location information regarding the target. For example, the moving robot 100 may set an area within a predetermined radius from the stored location information as a non-travelable area, and an area outside the radius as a travelable area.

Here, the predetermined radius may be determined in correspondence with an average size of the target. In addition, the predetermined radius may be set or changed through a user input. For example, in a state where a map on which a location of a target point is displayed is output on the display unit 151 of the terminal 200, the predetermined radius may vary through a touch gesture applied to the displayed location of the target point.

As described above, according to the embodiment of the present disclosure, in the case where there is a target, such as a temporary obstacle, which the moving robot has to temporarily avoid during travel, the target can be registered quickly using only the terminal 200 without performing avoidance design every time and making the moving robot travel along an outer periphery of the target, which may result in achieving user convenience and smooth travel of the moving robot 100. In addition, a location of a target can be calculated simply by pointing to the target using the terminal at a remote distance without having to move the terminal 200 to the location of the target, which may result in reducing the user's effort and time.

Hereinafter, description will be given in detail of embodiments of a method of calculating a location of a target point pointed using the terminal 200, with reference to FIGS. 6, 7A, and 7B.

Figure 6:
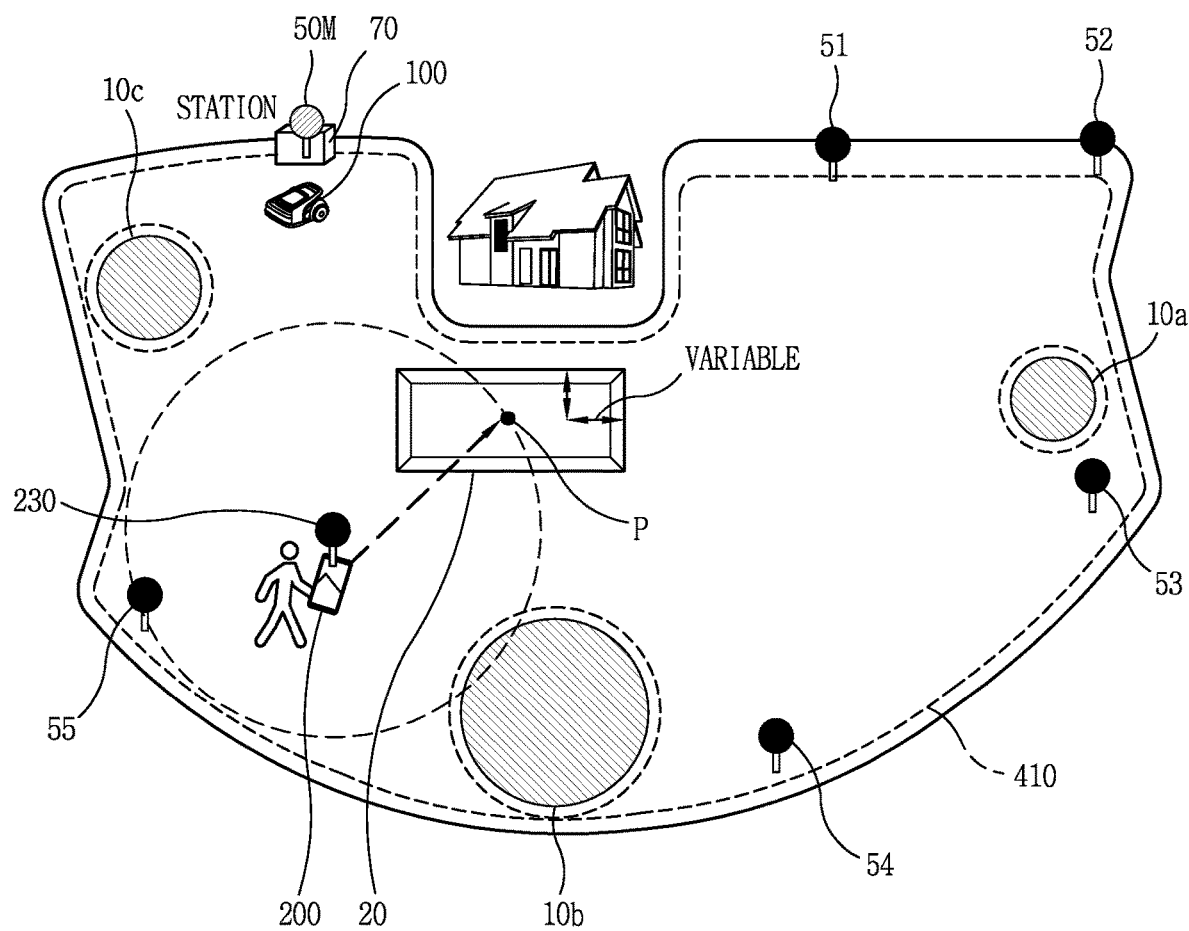
FIG. 6 is a conceptual view related to a method of calculating a location of an obstacle using the terminal within the boundary, in accordance with an embodiment of the present disclosure.

Referring to FIG. 6, a plurality of fixed obstacles 10a, 10b, and 10c existing in a travel area (or wireless area) 410 set within a boundary R may be registered.

At this time, locations of the plurality of fixed obstacles 10a, 10b, 10c may be registered on a map based on a reference location, for example, the location of the charging station 70.

For example, the moving robot 100 may set additional boundaries while moving along outer peripheries of the obstacles 10a, 10b, and 10c. Accordingly, an outer area of the additional boundary set at the outer periphery of each of the obstacles 10a, 10b, 10c may be set as a travelable area, and an inner area of the additional boundary may be set as a non-travelable area.

Alternatively, the obstacles 10a, 10b, and 10c may be registered on a map by receiving location information from location information transmitters which may be installed close to the respective obstacles 10a, 10b and 10c.

Next, for registering a target 20 such as a temporary obstacle, the main body of the terminal 200 may be tilted toward the target 20 at an arbitrary location within the boundary R and the terminal 200 may transmit a UWB signal toward the target. That is, pointing to the target 20 may be performed.

It may not matter that the terminal 200 and the target are located far away from each other. For example, the pointing according to the present disclosure can be performed even if the terminal 200 and the target are several meters (m) or several tens of meters (m) apart from each other within the boundary.

At this time, as the main body of the terminal 200 is tilted, a virtual straight line that the signal transmitted from the front of the main body of the terminal 200 is directed to the ground may be generated. The tilt of the main body of the terminal 200 may be adjusted such that the virtual straight line is on a central point P of the target 20.

Length, width, and height of the target 20 may vary. If the target 20 is an object having a predetermined height, the UWB signal transmitted from the terminal 200 may pass through the target.

The terminal 200 may determine its current location based on signals, for example, UWB signals, transmitted from the plurality of location information transmitters 50M, and 51 to 55.

While the terminal 200 is pointing to the target, the terminal 200 may sense movement change in a space through sensors. Specifically, the terminal 200 may determine the location of the target by sensing the movement change in a space corresponding to the pointing by using the gyro sensor and the acceleration sensor which are provided in the terminal 200, or the IMU sensor provided in the terminal 200.

Therefore, even if the terminal 200 is far from the target 20, the terminal 200 can determine the location of the target quickly by sensing the movement change in the space corresponding to the pointing, as long as the terminal 200 exists within the boundary R.

The moving robot 100 may receive coordinates information regarding a point that the terminal 200 is pointing at its current location.

The control unit of the moving robot 100 may determine a current location of the main body of the moving robot 200 based on signals (e.g., UWB signals) sent from the neighboring location information transmitters, and recognize coordinates of a target point, which matches the received location information, based on the determined location of the main body and the location of the terminal 200 existing within the boundary R.

That is, the control unit of the moving robot 100 may convert the location information received from the terminal 200 into coordinates with respect to the current location of the moving robot 100.

Hereinafter, different methods of determining (recognizing) the location of the target point pointed at by the terminal 200 will be described in detail with reference to FIGS. 7A and 7B.

Figure 7A:
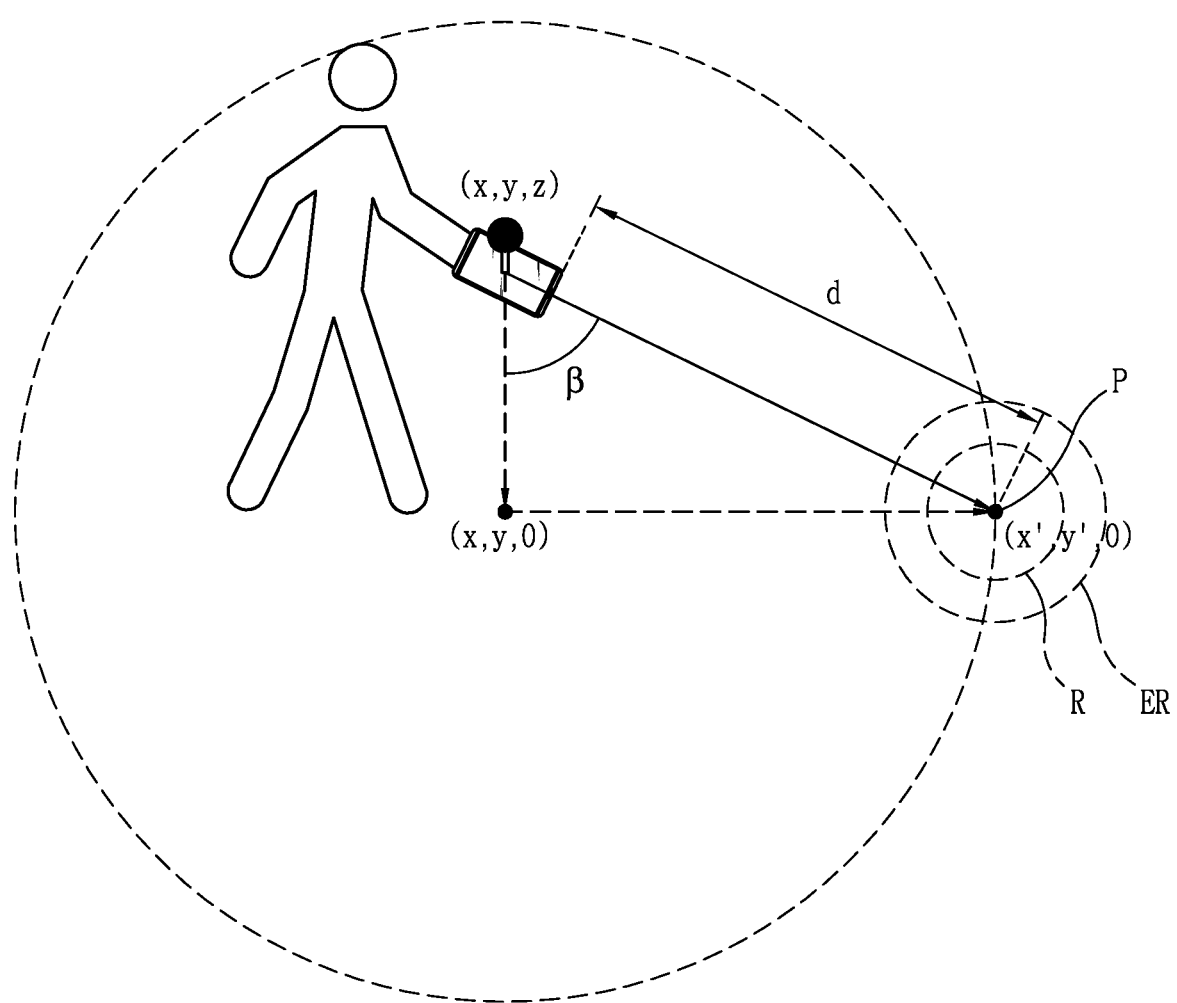
FIG. 7A is another conceptual view related to an exemplary method of calculating a location of an obstacle using the terminal within the boundary, in accordance with an embodiment of the present disclosure.

First, FIG. 7A illustrates that the terminal 200 calculates location information regarding to a target point by pointing to the target at its current location and transmits the location information to the moving robot 100.

The embodiment of FIG. 7A illustrates a case where the terminal 200 directly points to the target without trigger pointing to a reference location.

Here, the trigger pointing may mean a start operation for setting an initial posture value before pointing to a desired target. This trigger pointing may be performed, for example, for a reference location within the set boundary R or for the moving robot 100.

When pointing to the target is performed without the trigger pointing, a signal, for example, a UWB signal emitted from the terminal 200 may be directly received at the target.

Even if the trigger pointing is not performed, the current location of the terminal 200 may be recognized through a plurality of location information transmitters or GPS, and a bottom point of the current location of the terminal 200, namely, a point at which the z axis value is '0' may be set as a zero point.

Upon pointing to the target, the posture value of the terminal, namely, the x, y, z axis values may be a reference point for calculating an angle beta 13 needed to calculate a location of a target point pointed at by the terminal 200.

The x, y, and z values may be sensed using the six-axis gyro sensor and the six-axis acceleration sensor, or the IMU sensor, which are provided in the terminal 200, and the angle beta 13 may be calculated based on the sensed x, y, and z values. In addition, a distance d may be recognized based on the UWB signal transmitted from the terminal 200 to the target.

Since the change of the z axis value, the angle beta 13, and the distance d, which correspond to the movement of the terminal in a space can be determined, the terminal 200 may calculate coordinates (x', y', 0) corresponding to the location P of the target point (the bottom point of the target) with respect to its current location.

An area R having a predetermined radius centering on the calculated coordinates (x', y', 0) may be defined as 'target.' Alternatively, an area ER having a larger radius centering on the coordinates (x', y', 0) may be defined as a target through a user input or the like depending on the size of the target.

Meanwhile, the location information of the target point calculated by the terminal 200 may be directly reflected to the map of the moving robot 100 stored in the terminal 200 or transmitted to the moving robot 100.

Since the moving robot 100 and the terminal 200 are located at different locations, the control unit of the moving robot 100 may recognize coordinates corresponding to the location information regarding the target point with respect to the current location of the moving robot 100, on the basis of the distance information d regarding the target point pointed to at the location of the terminal 200, and a virtual trajectory (a large circle of FIG. 7A) generated centering on the location of the terminal 200.

That is, it can be recognized that the location of the target pointed by the terminal 200 is located at one point on the virtual trajectory.

On the other hand, since the location of the terminal 200 can be calculated through the plurality of location information transmitters upon pointing to the target, the x and y coordinates of the target point with respect to the current location of the moving robot 100 can be calculated when the terminal 200 transmits its location information together with the location information regarding the target point to the moving robot 100.

Figure 7B:
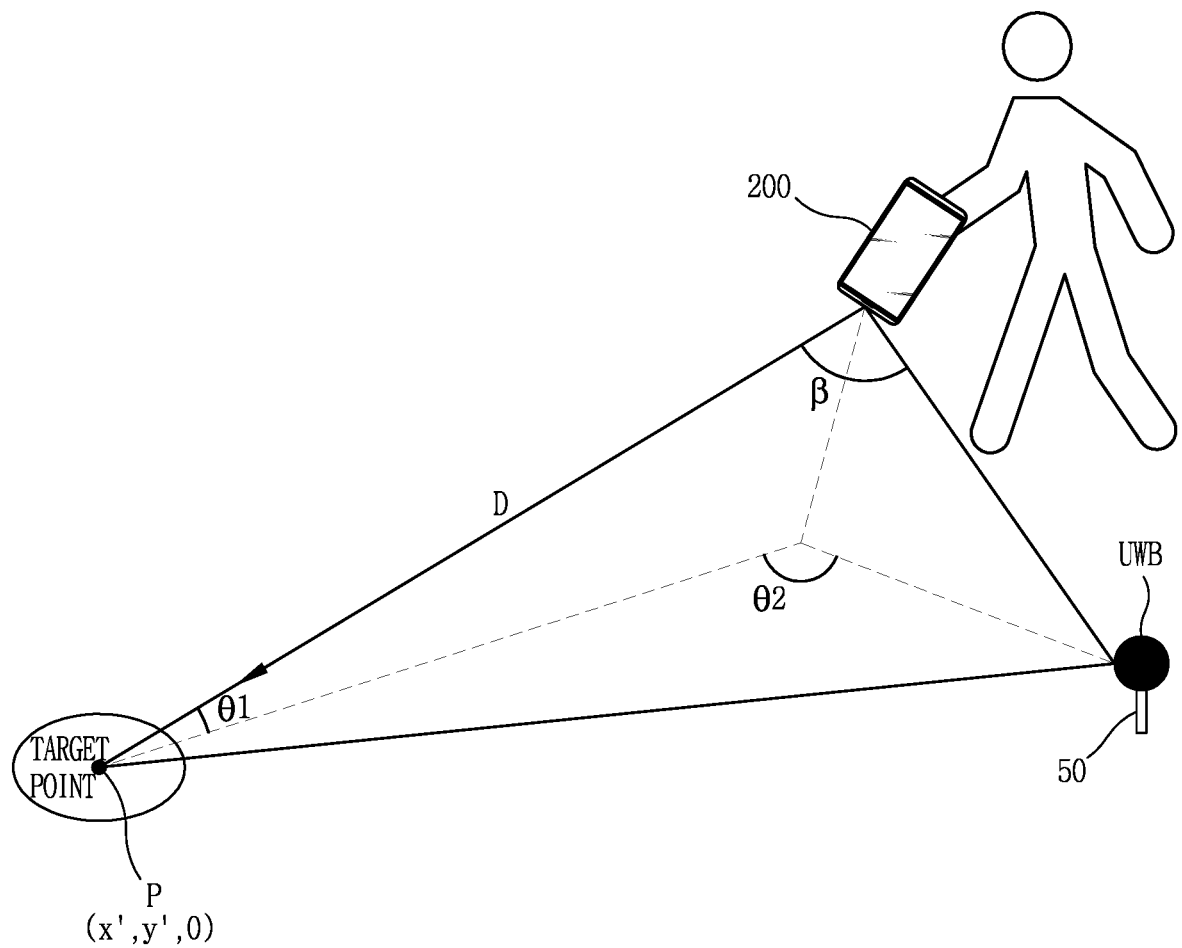
FIG. 7B is another conceptual view of the exemplary method of FIG. 7A, in accordance with an embodiment of the present disclosure.

Next, the embodiment of FIG. 7B illustrates a case where the terminal 200 points to a target after performing trigger pointing to a reference location.

Here, the reference location may be a reference point for setting an initial posture value of the terminal 200 before pointing to the target. The reference location may be, for example, the current location of the terminal within the boundary R, the location of the location information transmitter 50, the location of the charging station, or the location of the moving robot 100.

When the trigger pointing to the reference location is performed with respect to the moving robot 100, the moving robot 100 may receive a signal from the terminal 200 in a stopped state.

When the trigger pointing to the reference location is performed with respect to a specific location information transmitter, a height value of the ground, which has been set at installation of the location information transmitter, may be reflected in a height error correction of the location information regarding the target.

For example, in view of the characteristics of the outdoor environment, height of the ground may be uneven and height of a user who carries the terminal 200 may also be different. Due to this difference in height, a posture value of the main body may change when the terminal 200 points to the target. Accordingly, there may be a great error between coordinates of a target point calculated by the terminal 200 and coordinates of an actual target point.

When the terminal 200 performs trigger pointing to a location information transmitter, in which a height value of the ground has been reflected in advance, and then performs pointing to the target, 1) coordinates of the target point with respect to the current location of the terminal 200, and 2) coordinates of the target point with respect to the location of the location information transmitter, namely, a reference location may be calculated, respectively.

Thereafter, the terminal 200 may perform the height error correction based on the calculated coordinates 1) and 2), which may allow the coordinates of the target point to be more correctly calculated even if the terminal 200 points to the target at a farther distance.

On the other hand, if the pointing to the target is not performed within a predetermined time after the trigger pointing, the trigger pointing may be performed again.

Since the coordinates information related to the location information transmitter as the reference location is already known, 1) coordinates of the target point with respect to the current location of the terminal 200, and 2) coordinates (x', y', 0) of the target point with respect to the location of the location information transmitter as the reference location may be calculated, respectively, based on a first posture value of the terminal 200 performing the trigger pointing to the location information transmitter, a distance between the terminal 200 and the location information transmitter, a second posture value of the terminal 200 pointing to the target, and a distance between the terminal 200 and the target point.

Specifically, in FIG. 7B, a first angle θ1, a second angle θ3, and a third angle β may be calculated in the following manner. First, the third angle β is an angle between a line connecting the terminal 200 and the ground and a line connecting the terminal 200 and the location information transmitter 50. When the terminal 200 emits a signal to the location information transmitter 50, an angle between a reference line of a geomagnetic axis and an extension line from the terminal 200 to the location information transmitter 50 may be calculated using the six-axis gyro sensor and the six-axis acceleration sensor provided in the terminal 200, or the IMU sensor provided in the terminal 200. Then, by subtracting the calculated angle from 90 degrees, the third angle β may be obtained.

The first angle θ1 may be an angle between a reference line of the geomagnetic axis and an extension line in which the terminal 200 points to the target. When the signal is emitted as the terminal 200 points to the target, an angle between the line connecting the terminal 200 and the ground and the line in which the terminal 200 points to the target, may be calculated by using the six-axis gyro sensor and the six-axis acceleration sensor provided in the terminal 200, or the IMU sensor provided in the terminal 200. Then, by subtracting the calculated angle from 90 degrees, the first angle θ1 may be obtained.

The second angle θ2 is an angle, namely, a rotation angle between the line connecting the terminal 200 and the location information transmitter 50 and the line in which the terminal 200 points to the target. This angle may be calculated based on variations of yaw and pitch sensed in the terminal 200, using a posture value at a time point, at which the terminal 200 faces the location information transmitter 50, as a zero point.

Since distance information D between the terminal 200 and the target point and the angles θ1, θ2, β illustrated in FIG. 7B can be determined, coordinates of the target point with respect to the location information transmitter 50 can be calculated by multiplying the distance information D from the terminal 200 to the target point P and a coordinate transformation matrix formed by coordinate information of the terminal 200 which is acquired with the location information transmitter as a zero point.

On the other hand, this may be equally applied even when the reference position is the moving robot 100 other than the location information transmitter.

The control unit of the moving robot 100 may determine coordinates corresponding to the location information regarding the target point with respect to the current location of the moving robot 100, based on a first point corresponding to a reference location to which the terminal 200 has pointed at the current location, and a second point corresponding to the target point to which the terminal 200 has pointed at the current location.

Alternatively, the moving robot 100 may receive coordinates of a final target point, from which height error has been corrected based on location information (i.e., the second point) related to the target point calculated with respect to the first point, and location information (i.e., the second point) related to the target point calculated with respect to the current location of the terminal 200, and recognize coordinates of the target point with respect to the current location of the moving robot 100.

On the other hand, the embodiment illustrated in FIG. 7A may be suitable when the location of the terminal 200 is relatively close to a target because operation and calculation are simple but a slight height error may possibly occur, and the embodiment illustrated in FIG. 7B can be useful even when the location of the terminal 200 is relatively far from a target because no height error occurs although additional operations are required.

Figure 8:
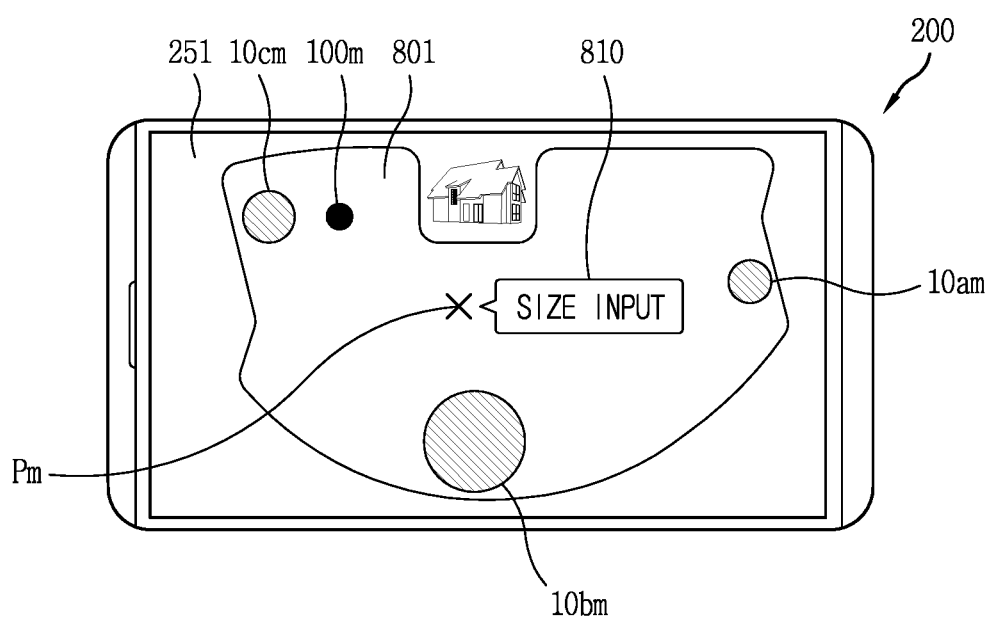
FIG. 8 is a view illustrating an exemplary screen in which locations of the moving robot and obstacles are displayed inside the boundary, in accordance with an embodiment of the present disclosure.

FIG. 8 illustrates an exemplary screen in which calculated location information regarding a target point is displayed on the display unit 251 of the terminal 200. At this time, the terminal may not have to be located within a boundary and it may be sufficient for the terminal 200 to perform communication with the moving robot 100 or a server associated with the control of the moving robot 100.

The terminal 200 and the moving robot 100 may perform wireless communication such as UWB communication, Bluetooth, ZigBee, WIFI, RFID, and the like.

The terminal 200 may be provided with an application installed therein for controlling the moving robot 100. When an application execution command is input by a user operation, the terminal 200 may determine whether communication with the moving robot 100 is available, and output an application execution screen on the display unit 251.

For example, as illustrated in FIG. 8, a boundary set for the moving robot 100 and a map screen showing a travel area set based on the boundary may be output on the display unit 251 of the terminal 200.

On the other hand, when there are a plurality of moving robots capable of performing communication, and a plurality of maps is stored for one moving robot, a user interface (UI) for selecting a moving robot and a map may be displayed on the display unit 251 of the terminal 200.

Image objects 10am, 10bm, 10cm corresponding to registered fixed obstacles may be displayed inside a travel area 801 of a map screen. Then, a moving robot image 100m corresponding to the current location of the moving robot 100 may be displayed in real time.

For this purpose, the terminal 200 may receive location information related to the moving robot 100, which may be recognized based on signals transmitted from a plurality of location information transmitters, from the moving robot 100 in real time.

Also, a target Pm corresponding to the location information regarding the target point calculated with reference to FIGS. 7A and 7B may be displayed inside the travel area 801 on the map screen. At this time, a pop-up window 810 for requesting input of the size of the target may be output adjacent to the target Pm. Alternatively, the pop-up window 810 may be output if a touch input is applied to the displayed target Pm.

When a touch input is applied to the pop-up window 810, a process for inputting the size of the target may be initiated. Accordingly, a target size setting screen may be output to the display unit 251.

Meanwhile, although not shown, when identification information related to the target Pm is included, the terminal 100 may automatically search for size information and/or shape information related to the target Pm corresponding to the identification information, and download an associated application from a server. Here, the identification information refers to product information for immediately searching for size information and/or shape information regarding the target on a web.

When the size information and/or shape information regarding the target are automatically downloaded, a target image corresponding to the size and/or shape of the target Pm may be displayed on a map screen and a boundary corresponding to the size and/shape of the target Pm may be automatically set.

The moving robot 100 may receive, from the terminal 200, the size information and/or the shape information of the target Pm or the boundary information of the target Pm. Then, the received size information and/or shape information or boundary information are applied to the stored location information. Then, the inside of the boundary of the target Pm may be set as a non-travelable area and the outside of the boundary of the target Pm may be set as a travelable area.

Figure 9A:
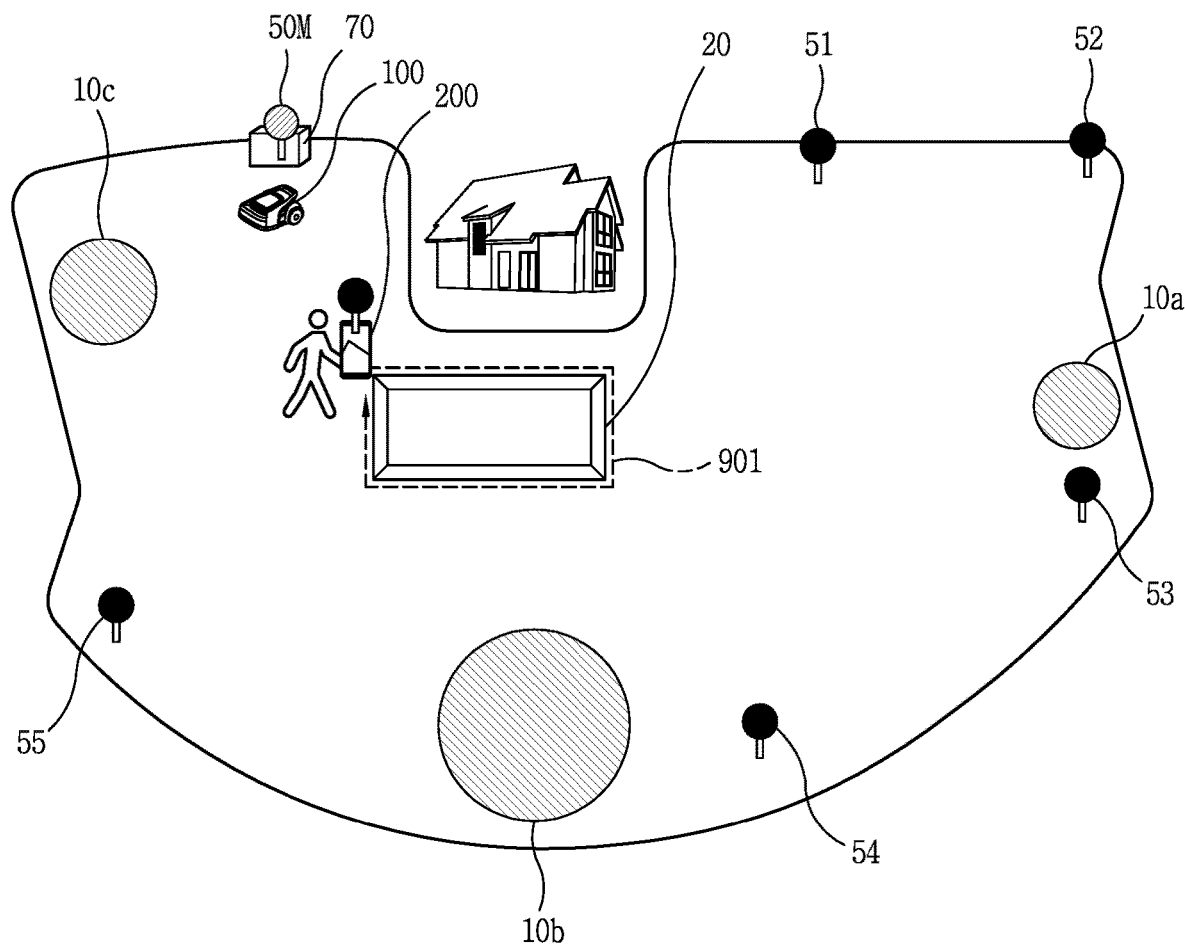
FIG. 9A is a conceptual view illustrating an exemplary method for setting a boundary of an obstacle using a terminal, in accordance with an embodiment of the present disclosure.
Figure 9B:
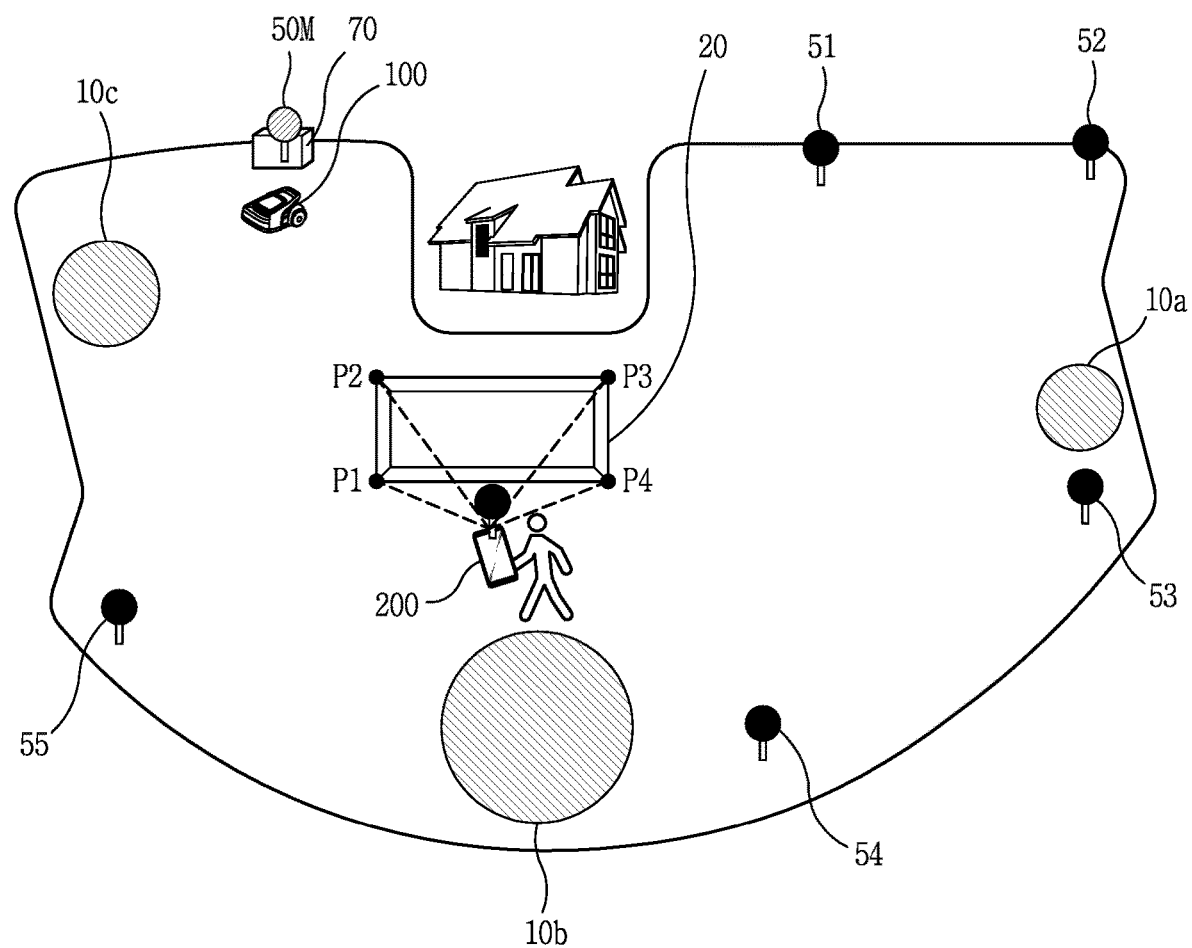
FIG. 9B is another conceptual view illustrating an exemplary method for setting a boundary of an obstacle using a terminal, in accordance with an embodiment of the present disclosure.

On the other hand, in the case where the identification information related to the target is not included, the size information or shape information regarding the target can be obtained through the embodiment illustrated in FIGS. 9A and 9B.

First, as one embodiment, referring to FIG. 9A, a target 20 may be pointed using the terminal 200. Then, a virtual target boundary 901 may be set based on a change in location of the terminal 200 which is moving along an outer periphery of the target 20.

Specifically, the terminal 200 may move to a location where the actual target 20 is located, and then move along the outer periphery of the target 20 from an arbitrary point. While the terminal 200 moves along the outer periphery of the target 20, coordinates corresponding to a changed position, which may be recognized based on signals transmitted from the plurality of location information transmitters 50M, and 51 to 55 may be stored in a sequential manner.

For example, amounts/intensities of the UWB signals transmitted from the UWB module provided in the terminal 200 and the UWB signals transmitted from the plurality of location information transmitters 50M and 51 to 55 may be analyzed to determine the current position of the terminal 200 which is moving within the boundary R.

When a closed loop shape in which a start point and an end point become the same as the terminal 200 returns to the arbitrary point, points corresponding to the stored location information may be connected by one line so as to set a virtual target boundary 901 corresponding to a moving path of the terminal 200. The virtual target boundary may be used as the same meaning as a boundary of a predetermined area including coordinates of a target point pointed by the terminal 200.

The moving robot 100 may be located anywhere within the boundary R. That is, the moving robot 100 may receive the location information sequentially stored in the terminal 200 from the terminal 200 to directly set the target boundary, or may receive the information related to the target boundary directly from the terminal 200.

When the target boundary is set in this way, size information and/or shape information regarding the target may be registered on the map. Then, the control unit of the moving robot 100 may control the traveling unit to move in the travel area without entering the set target boundary while traveling in the travel area.

The moving robot 100 may set the inside of the target boundary as a non-travelable area and the outside of the target boundary as a travelable area.

In the case where the target is not in a designated shape, for example, a circle, a rectangle, or the like, it may facilitate the terminal 200 to set a more accurate target boundary by moving to the actual location of the target 20.

However, such a method may be sufficiently realized by only the movement of the terminal 200 but it may be assumed that the terminal 200 is moved to the actual location of the target 20 by a user or the like. Hereinafter, another method for obtaining size information and/or shape information regarding a target will be described with reference to FIG. 9B.

As another embodiment, referring to FIG. 9B, a target may be pointed by using the terminal 200. Afterwards, a plurality of points that the terminal 200 consecutively points to corners of the target may be sequentially connected to set a virtual target boundary.

Specifically, the terminal 200 may sequentially point to corners of the target in one diction, for example, in a clockwise or counterclockwise direction, without moving at a spot which is pointed by the terminal 200 to acquire location information related to a target point.

The process of calculating location information for each pointed point is the same as that described in the method for calculating the location information of the target point, and thus description thereof will be omitted here.

In FIG. 9B, the terminal 200 may acquire coordinates information related to each of corners P1, P2, P3, and P4, namely, a plurality of target points of the target, through signals transmitted from the plurality of location information transmitters, the six-axis gyro sensor and the six-axis acceleration sensor or the IMU sensor provided in the terminal 200, and the UWB sensor of the terminal 200.

The terminal 200 may store the coordinates information regarding the corners P1, P2, P3, and P4, and may set a target boundary based on the stored coordinates information.

In FIG. 9B, the coordinates information for the four corners may be obtained on the assumption that the shape of the target is a rectangle. However, the number of corners may be smaller or greater than four depending on the shape of the target.

In the embodiment of FIG. 9B, the coordinates information for setting the target boundary may be collected at the point where the terminal 200 has first pointed to the target, without moving to the actual location of the target 20. This may result in quickly acquiring the location information and size information and/or shape information regarding the target even at a far distance.

Meanwhile, the moving robot 100 may receive the location information regarding the corners, sequentially stored in the terminal 200, from the terminal 200 to directly set the target boundary, or may receive the information related to the target boundary directly from the terminal 200.

When the target boundary is set in this way, size information and/or shape information regarding the target may be registered on the map. Then, the control unit of the moving robot 100 may control the traveling unit to move in the travel area without entering the set target boundary, or along the target boundary while traveling in the travel area.

To this end, the moving robot 100 may set the inside of the target boundary as a non-travelable area and the outside of the target boundary as a travelable area.

Such different methods for obtaining size information of a target may be determined differently depending on a shape of a target to be registered. For example, the embodiment illustrated in FIG. 9A may be applied when a target has a complicated shape or when a target has too many corners, while the embodiment illustrated in FIG. 9B may be applied when a target is large in size or simple in shape or when a target is not a fixed object, namely, is a temporary obstacle (e.g., temporary trap area).

Figure 10:
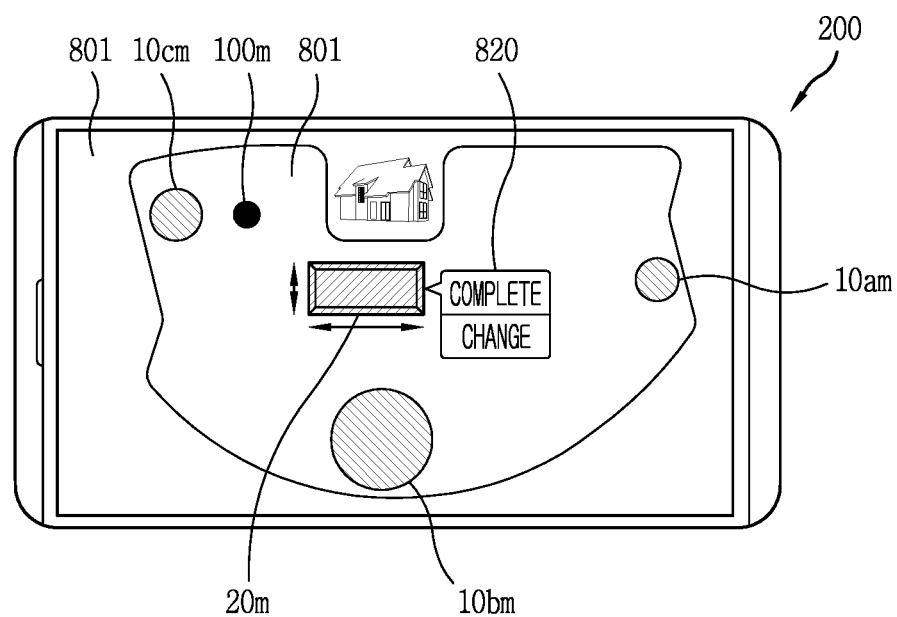
FIG. 10 is a conceptual view illustrating an exemplary screen in which size information related to the obstacle is displayed within the boundary, in accordance with an embodiment of the present disclosure.

FIG. 10 illustrates an exemplary screen of a display unit 251 of the terminal 200 on which size information regarding a target may be displayed.

Referring to FIG. 10, it can be seen that image objects 10*am*, 10*bm*, and 10*cm* indicating fixed obstacles and a target 20*m* to which location and size have been reflected may be displayed in a travel area 801 of a map screen for the moving robot 100.

To this end, when the moving robot 100 is in a state of being capable of performing communication with the terminal 200, size information regarding a target may be transmitted to the terminal 200, based on the change in location of the terminal 200, which points to the target and then moves along the outer periphery of the target, or a virtual target boundary which is set in a manner of connecting a plurality of points consecutively pointed by the terminal 200. Alternatively, the target size information may be displayed based on target size information stored in the terminal 200 or by receiving from a server associated with the control of the moving robot 100.

A moving robot image 100*m* indicating the current location of the moving robot may also be displayed in the travel area 801. For this, in one embodiment, when the moving robot 100 can perform communication with the terminal 200, the moving robot may transmit its location information to the terminal 200 together with location information related to a target point stored in the moving robot itself.

In FIG. 10, when the target 20*m* to which the target size information is reflected is displayed, a pop-up window 820 for confirming whether or not to register the corresponding size information in a location adjacent to the target 20*m* may be output.

For example, when a menu 'Complete' is selected in the pop-up window 820, the registration of the target based on the current size information may be completed. When a menu 'Change' is selected in the pop-up window 820, the displayed screen may switch to a user interface (UI) screen for changing the size information of the target. In this case, although not illustrated, the size information of the target can be changed by applying a touch gesture to the target 20*m* through the switched UI screen, or by the method described with reference to FIGS. 9A and 9B.

Hereinafter, description will be given of an embodiment related to changing or removing a registered target according to various environmental changes after registering location and size information of the target, with reference to FIGS. 11A to 11C.

In the present disclosure, since it is premised that the target exists temporarily, its location may change. When the target changes only in location, the terminal 200 may perform pointing to the changed location (the center of the target) and then calculating location information regarding the changed target point. Then, the location information of the changed target point may be transmitted to the moving robot 100 together with a target location information change request.

Then, the control unit of the moving robot 100 may change prestored location information of the target, in response to the target location information change request received from the terminal 200.

While the moving robot 100 is moving in the travel area, the traveling unit may be controlled so that the current location of the main body of the moving robot 100, which has been determined according to the signals transmitted from the location information transmitters, is not included in an area corresponding to the changed location information.

Since size information is the same when the target is changed only in location, the control unit of the moving robot 100 can immediately set a target boundary and a corresponding non-travelable area based on prestored size information if only the changed location information of the target is received from the terminal 200.

Figure 11A:
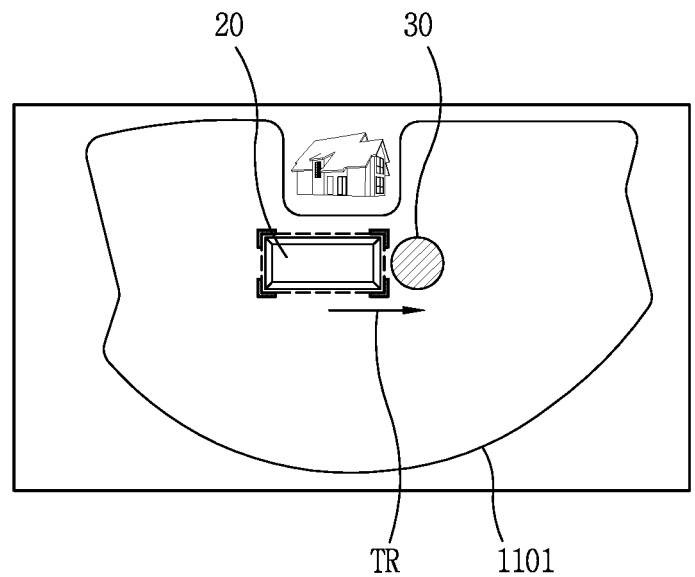
FIG. 11A is a conceptual view illustrating an example of a method of quickly changing registered obstacle information, in accordance with to an embodiment of the present disclosure.
Figure 11B:
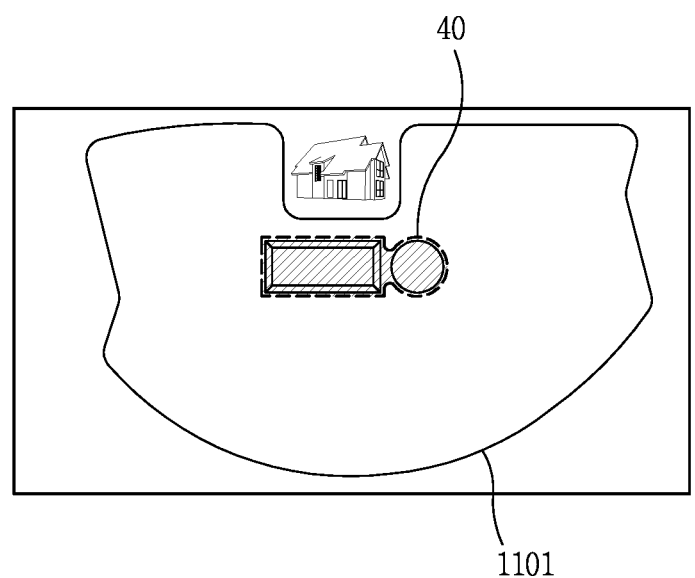
FIG. 11B is another conceptual view of the exemplary method of FIG. 11A, in accordance with to an embodiment of the present disclosure.

As another example, FIGS. 11A and 11B illustrate an exemplary embodiment of changing target size information by combining the target and obstacles adjacent to the target, according to detection and registration of the adjacent obstacles after the registration of the target.

As illustrated in FIG. 11A, when an obstacle 30 which is adjacent to a pre-registered target 20 within a predetermined distance is additionally registered on a travel area 1101, the target and the additionally-registered obstacle may be merged into one obstacle in response to a merge request.

At this time, the merge request may be generated by, for example, a method in which a touch input applied to any one of the target and the additionally-registered obstacle illustrated in FIG. 11A is dragged (TR) to the other. In addition, the merge request may be generated through an input (e.g., an input of a changed size value or setting of a changed target boundary) to a setting screen of a stored map.

When such a merge request is received, an extended target 40, in which the target and the additionally-registered obstacle are merged into one, may be set, as illustrated in FIG. 11B. Accordingly, the target boundary and a boundary set for the additionally-registered obstacle may be modified into one closed loop boundary, which may then be set as a boundary of the extended target 40.

Now, the moving robot 100 may travel along an outer periphery of the extended target 40 and the inside of the extended target 40 may be set as a non-travelable area.

Figure 11C:
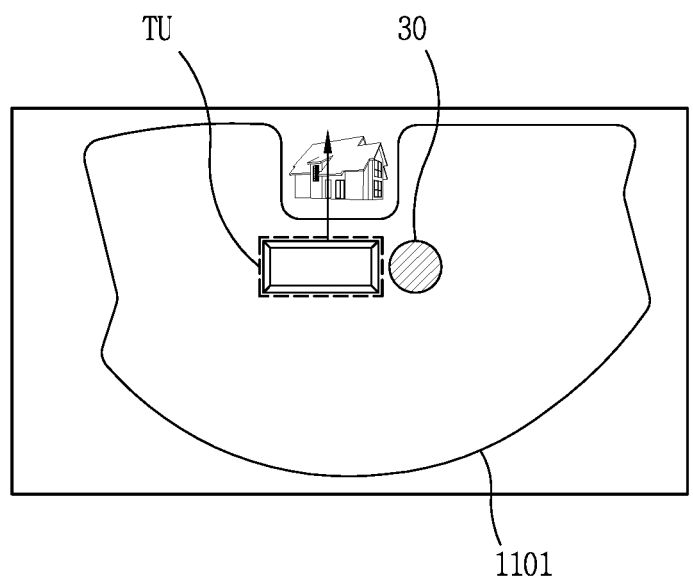
FIG. 11C is another conceptual view of the exemplary method of FIG. 11A, in accordance with to an embodiment of the present disclosure.

As another example, FIG. 11C illustrates an example of deleting a pre-registered target. At this time, there may be an additionally-registered obstacle 30 after registration of a target. A target that is temporarily present may be removed from an area after a predetermined period of time elapses. In this case, a target registered on a map may also be removed.

For example, as illustrated in FIG. 11C, a target registered on a map may be quickly removed by performing a preset touch gesture with respect to a pre-registered target 20 displayed within a travel area 1101, for example, a flicking touch gesture or a drag touch gesture applied upward on a screen, or a flick touch gesture or a drag touch gesture applied downward on a screen.

Alternatively, a pre-registered target may be removed from a map by various methods of deleting an application icon from the terminal 200, for example, selecting a mark 'x' appearing after a long touch input or performing a gesture of moving a target image to a removal area appearing after a long touch input.

FIG. 12 is an overall flowchart for controlling the operation of the moving robot 100 based on location information and size information regarding a target obtained using the terminal 200.

Referring to FIG. 12, a virtual boundary and a travel area with respect to the boundary may be set (S1210). Next, a location of the terminal may be recognized and location information related to a target point to which the terminal has pointed at the recognized location may be received from the terminal (S1220).

After pointing to the target, a plurality of points corresponding to the change in location of the terminal, which is moving along an outer periphery of the target point, or a plurality of points to which the terminal has consecutively pointed may be received from the terminal and stored (S1230).

Location information regarding an initially-pointed target point may be received together with information corresponding to the plurality of points.

Next, the plurality of points may be connected to set a boundary, namely, a target boundary for a predetermined area including coordinates that match the location information regarding the initially-pointed target point (S1230).

Once the target boundary is set as described above, the target corresponding to the target boundary may be registered on a map associated with the travel of the moving robot.

Next, the moving robot may determine whether the set target boundary is recognized while moving in the travel area (S1240). While the set target boundary is not recognized, the moving robot may determine it as a travelable area and perform a preset operation, for example, travel with avoiding obstacles, which are detected during the travel, according to a preset travel path (or according to a pre-planned travel manner) (S1250).

On the other hand, when it is determined that the set target boundary has been recognized, the moving robot may determine the inside of the target boundary as a non-travelable area, and thus travel without entering the target boundary or move along the target boundary (S1260).

As described above, according to an embodiment of the present disclosure, in the case where there is a target, such as a temporary obstacle, which the moving robot has to temporarily avoid during travel, the target can be registered quickly using only the terminal 200, which can be moved quickly, without performing an avoidance design every time or making the moving robot travel along an outer periphery of the target. This may result in achieving user convenience and smooth travel of the moving robot 100. In addition, since a location of a target can be calculated by simply pointing to the target by the terminal at a far distance without moving the terminal to the location of the target, the user's effort and time can be reduced. In addition, acquisition of a size of a target and registration, change and removal of the target corresponding to the size can be simply performed selectively by making the terminal move along an outer periphery of the target or additionally pointing to corners of the target at a remote distance.

The present disclosure described above can be implemented as computer-readable codes on a program-recorded medium. The computer readable medium includes all kinds of recording devices in which data readable by a computer system is stored. Examples of the computer-readable medium include a hard disk drive (HDD), a solid state disk (SSD), a silicon disk drive (SDD), a ROM, a RAM, a CD-ROM, a magnetic tape, a floppy disk, an optical data storage device and the like, and may also be implemented in the form of a carrier wave (e.g., transmission over the Internet). In addition, the computer may also include the control unit 1800 of the moving robot. The above detailed description should not be limitedly construed in all aspects and should be considered as illustrative. The scope of the present disclosure should be determined by rational interpretation of the appended claims, and all changes within the scope of equivalents of the present disclosure are included in the scope of the present disclosure.

What is claimed is:

1. A moving robot comprising:
   a main body;
   a driving motor including at least one wheel configured to move the main body by rotating the at least one wheel;
   a communication unit configured to communicate with a location information transmitter and a terminal through a wireless communication scheme, the location information transmitter being installed in an area to transmit a signal; and
   a controller configured to set a travel area based on a virtual boundary, the virtual boundary being set using location information based on a signal received from the location information transmitter,
   wherein the controller is configured to recognize a location of the terminal and store location information related to a target point, the target point being located within the virtual boundary and pointed by the terminal at the recognized location,
   wherein the controller is configured to control the driving motor such that the main body avoids a predetermined area comprising coordinates that match the stored location information while moving in the set travel area, and
   wherein the controller is further configured to recognize coordinates of the target point corresponding to the location information relative to a current location of the main body, based on:
      a first point corresponding to a reference location pointed by the terminal at the current location of the terminal, and
      a second point corresponding to the target point pointed by the terminal at the current location after pointing to the first point.

2. The moving robot of claim 1, wherein the target point corresponds to single coordinates, pointed by the terminal, among a plurality of coordinates that match temporary obstacles or specific areas to be set as non-travelable areas within the travel area.

3. The moving robot of claim 1, wherein:
   the controller is further configured to recognize a current location of the terminal based on the signal transmitted from the location information transmitter, and
   the controller is further configured to receive, as the location information, coordinates of the target point, the coordinates being calculated relative to the recognized current location of the terminal.

4. The moving robot of claim 1, wherein:
   the controller is further configured to determine a current location of the main body based on the signal transmitted from the location information transmitter, and
   the controller is further configured to recognize coordinates of the target point corresponding to the received location information, based on the determined location of the main body and the location of the terminal existing within the virtual boundary.

5. The moving robot of claim 1, wherein:
   the second point corresponds to the coordinates of the target point calculated based on the terminal,
   the first point corresponds to coordinates of one of the current location of the terminal, a location of the location information transmitter, a location of the moving robot, or a location of a charging station of the moving robot, and
   an initial posture value of the terminal is set based on the first point before pointing to the second point.

6. The moving robot of claim 1, wherein the controller is further configured to recognize coordinates of the target point corresponding to the location information relative to a current location of the main body, based on:
   a distance information between the location of the terminal and the target point, and
   a virtual trajectory generated based on the location of the terminal.

7. The moving robot of claim 1, wherein:
   the controller is further configured to set a boundary of the predetermined area based on a change in the location of the terminal, the location of the terminal being movable along a periphery of the target point after pointing to the target point, and the controller is further configured to control the driving motor such that the main body moves along the boundary of the predetermined area and moves in the travel area, without entering the boundary of the predetermined area.

8. The moving robot of claim 1, wherein:

the controller is further configured to set a boundary of the predetermined area by connecting a plurality of points continuously pointed by the terminal after pointing to the target point, and the controller is further configured to control the driving motor such that the main body moves along the boundary of the predetermined area and moves in the travel area, without entering the boundary of the predetermined area, when the boundary of the predetermined area is recognized.

9. The moving robot of claim 1, wherein the controller is further configured to transmit the stored location information and the location information of the main body to the terminal.

10. The moving robot of claim 1, wherein the controller is further configured to transmit at least one of size information or shape information associated with the target, based on a boundary of the predetermined area, the boundary of the predetermined area being set based on a change in location of the terminal that is movable along a periphery of the target point after pointing to the target point.

11. The moving robot of claim 1, wherein the controller is further configured to transmit at least one of size information or shape information associated with the target, based on a boundary of the predetermined area set by connecting a plurality of points consecutively pointed by the terminal after pointing to the target point.

12. The moving robot of claim 1, wherein:

the controller is further configured to update the stored location information to coordinates that match with a changed target point, in response to a target point change request received from the terminal, and the controller is further configured to control the driving motor such that a current location of the main body determined according to the signal of the location information transmitter while the main body is moving in the travel area is not included in a predetermined area comprising coordinates that match the updated located information.

13. The moving robot of claim 1, wherein, when an obstacle is detected near a predetermined area including coordinates that match the stored location information, the controller is further configured to control the driving motor to move while avoiding a merged area generated by merging the predetermined area with the detected obstacle.

14. A moving robot system comprising:

a location information transmitter installed in an area, the location information transmitter being configured to transmit a signal for recognizing location information;

a moving robot configured to set a virtual boundary relative to location information, based on a signal received from the location information transmitter, and configured to move in a travel area set based on the virtual boundary; and a terminal configured to communicate with the location information transmitter within the virtual boundary, calculate location information regarding a pointed target point within the virtual boundary by using a signal, and transmit the location information to the moving robot, wherein the moving robot is further configured to store the transmitted location information regarding the target point and move in the travel area while avoiding a predetermined area comprising coordinates that match the stored location information, and wherein the moving robot is further configured to recognize coordinates of the target point corresponding to the location information relative to a current location of a main body of the moving robot, based on:

a first point corresponding to a reference location pointed by the terminal at the current location of the terminal, and a second point corresponding to the target point pointed by the terminal at the current location after pointing to the first point.

15. The moving robot system of claim 14, wherein:

the terminal is further configured to set a boundary of the predetermined area based on a change in location while moving along a periphery of the target point after pointing to the target point, the terminal is further configured to transmit information related to the set boundary of the predetermined area to the moving robot, and the moving robot is configured to move in the travel area while avoiding the boundary of the predetermined area.

16. The moving robot system of claim 14, wherein:

the terminal is further configured to set a boundary of the predetermined area by connecting a plurality of points continuously pointed after pointing to the target point, the terminal is further configured to transmit information related to the boundary of the predetermined area to the moving robot, and the moving robot is configured to move in the travel area along the boundary of the predetermined area without entering the boundary of the predetermined area.

17. A method for controlling a moving robot, the method comprising:

setting a virtual boundary relative to location information based on a signal received from a location information transmitter so as to set a travel area based on the virtual boundary;

recognizing a location of a terminal configured to communicate with a main body, to receive location information regarding a target point pointed by the terminal at the recognized location of the terminal;

storing the received location information; and moving in the travel area while avoiding a predetermined area comprising coordinates that match the stored location information, wherein the recognizing further comprises:

recognizing coordinates of the target point corresponding to the location information relative to a current location of the main body, based on:

a first point corresponding to a reference location pointed by the terminal at the current location of the terminal, and a second point corresponding to the target point pointed by the terminal at the current location after pointing to the first point.

* * * * *